(12) United States Patent
Karp et al.

(10) Patent No.: US 6,890,093 B2
(45) Date of Patent: May 10, 2005

(54) MULTI-STREAM MICROFLUDIC MIXERS

(75) Inventors: Christoph D. Karp, Pasadena, CA (US); Joseph F. Covington, San Gabriel, CA (US)

(73) Assignee: Nanostream, Inc., Pasadena, CA (US)

( * ) Notice: Subject to any disclaimer, the term of this patent is extended or adjusted under 35 U.S.C. 154(b) by 178 days.

(21) Appl. No.: 10/046,071

(22) Filed: Jan. 11, 2002

(65) Prior Publication Data

US 2002/0097633 A1 Jul. 25, 2002

Related U.S. Application Data

(63) Continuation-in-part of application No. 09/632,681, filed on Aug. 7, 2000, now abandoned.
(60) Provisional application No. 60/296,882, filed on Jun. 7, 2001.

(51) Int. Cl.$^7$ .............. B81B 1/00; B81B 7/00
(52) U.S. Cl. ............ 366/336; 366/341; 422/188; 422/100; 137/833
(58) Field of Search .......... 366/165.1, 165.2, 366/336, 337, 338, 340, 341; 422/129, 156, 188, 100; 137/814, 815, 833

(56) References Cited

U.S. PATENT DOCUMENTS

| | | | |
|---|---|---|---|
| 3,856,270 A | * 12/1974 | Hemker | 366/340 |
| 4,946,795 A | 8/1990 | Gibbons et al. | 436/179 |
| 5,070,606 A | 12/1991 | Hoopman et al. | 29/890.09 |
| 5,194,133 A | 3/1993 | Clark et al. | 204/299 R |
| 5,222,808 A | 6/1993 | Sugarman et al. | 366/274 |
| 5,230,866 A | 7/1993 | Shartle et al. | 422/103 |
| 5,376,252 A | 12/1994 | Ekstrom et al. | 204/299 R |
| 5,385,709 A | 1/1995 | Wise et al. | 422/98 |
| 5,443,890 A | 8/1995 | Ohman | 428/167 |

(Continued)

FOREIGN PATENT DOCUMENTS

| | | |
|---|---|---|
| EP | 0 107 631 A2 | 5/1984 |
| EP | 0 933 126 A1 | 8/1999 |
| EP | 1 123 734 A2 | 8/2001 |
| WO | WO 97/00125 | 1/1997 |
| WO | WO 97/12665 | 4/1997 |
| WO | WO 98/45693 | 10/1998 |
| WO | WO 98/56505 | 12/1998 |
| WO | WO 99/17093 | 4/1999 |
| WO | WO 99/17917 | 4/1999 |
| WO | WO 99/29497 | 6/1999 |
| WO | WO 99/60397 | 11/1999 |
| WO | WO 00/21659 | 4/2000 |
| WO | WO 00/22436 | 4/2000 |
| WO | WO 01/28670 | 4/2001 |
| WO | WO 01/025138 | 4/2001 |
| WO | WO 01/78893 | 10/2001 |
| WO | WO 02/10732 A1 | 2/2002 |

OTHER PUBLICATIONS

Strock, Abraham D. et al., "Chaotic Mixer for Microchannels," Science Magazine, vol. 295, pp. 647–651, Jan. 25, 2002.

(Continued)

Primary Examiner—Tony G. Soohoo
(74) Attorney, Agent, or Firm—Vincent K. Gustafson; Michael F. Labber

(57) ABSTRACT

Robust microfluidic mixing devices mix multiple fluid streams passively, without the use of moving parts. In one embodiment, these devices contain microfluidic channels that are formed in various layers of a three-dimensional structure. Mixing may be accomplished with various manipulations of fluid flow paths and/or contacts between fluid streams. In various embodiments, structures such as channel overlaps, slits, converging/diverging regions, turns, and/or apertures may be designed into a mixing device. Mixing devices may be rapidly constructed and prototyped using a stencil construction method in which channels are cut through the entire thickness of a material layer, although other construction methods including surface micromachining techniques may be used.

28 Claims, 21 Drawing Sheets

U.S. PATENT DOCUMENTS

| | | | |
|---|---|---|---|
| 5,534,328 A | 7/1996 | Ashmead et al. | 428/166 |
| 5,545,367 A | 8/1996 | Bae et al. | 264/401 |
| 5,595,712 A | 1/1997 | Harbster et al. | 422/129 |
| 5,640,995 A | 6/1997 | Packard et al. | 137/597 |
| 5,646,039 A | 7/1997 | Northrup et al. | 435/287.2 |
| 5,658,515 A | 8/1997 | Lee et al. | 264/219 |
| 5,690,763 A | 11/1997 | Ashmead et al. | 156/60 |
| 5,698,299 A | 12/1997 | Schmidt et al. | 428/209 |
| 5,771,810 A | 6/1998 | Wolcott | 101/483 |
| 5,842,787 A | 12/1998 | Kopf-Sill et al. | 366/340 |
| 5,846,396 A * | 12/1998 | Zanzucchi et al. | 422/103 |
| 5,849,208 A | 12/1998 | Hayes et al. | 216/94 |
| 5,858,188 A | 1/1999 | Soane et al. | 204/454 |
| 5,869,004 A | 2/1999 | Parce et al. | 422/100 |
| 5,872,010 A | 2/1999 | Karger et al. | 436/173 |
| 5,882,465 A | 3/1999 | McReynolds | 156/285 |
| 5,882,571 A | 3/1999 | Kaltenbach et al. | 264/400 |
| 5,904,424 A | 5/1999 | Schwesinger et al. | 366/336 |
| 5,904,824 A | 5/1999 | Oh | 204/601 |
| 5,921,678 A | 7/1999 | Desai et al. | 366/336 |
| 5,922,591 A | 7/1999 | Anderson et al. | 435/287.2 |
| 5,932,315 A | 8/1999 | Lum et al. | 428/172 |
| 5,932,799 A | 8/1999 | Moles | 73/53.01 |
| 5,945,203 A | 8/1999 | Soane | 428/209 |
| 5,985,119 A * | 11/1999 | Zanzucchi et al. | 204/450 |
| 6,004,515 A | 12/1999 | Parce et al. | 422/100 |
| 6,007,775 A | 12/1999 | Yager | 422/57 |
| 6,030,581 A | 2/2000 | Virtanen | 422/68.1 |
| 6,074,725 A | 6/2000 | Kennedy | 428/188 |
| 6,136,272 A | 10/2000 | Weigl et al. | 422/82.05 |
| 6,186,660 B1 | 2/2001 | Kopf-Sill et al. | 366/340 |
| 6,190,034 B1 | 2/2001 | Nielsen et al. | 366/336 |
| 6,193,471 B1 | 2/2001 | Paul | 417/53 |
| 6,235,471 B1 | 5/2001 | Knapp et al. | 435/6 |
| 6,264,900 B1 | 7/2001 | Schubert et al. | 422/224 |
| 6,287,520 B1 | 9/2001 | Parce et al. | 422/100 |
| 6,296,020 B1 | 10/2001 | McNeely et al. | 138/806 |
| 6,409,832 B2 | 6/2002 | Weigl et al. | 117/206 |
| 6,482,306 B1 | 11/2002 | Yager et al. | 204/600 |
| 6,494,614 B1 * | 12/2002 | Bennett et al. | 366/336 |
| 6,537,506 B1 * | 3/2003 | Schwalbe et al. | 422/100 |
| 6,572,830 B1 * | 6/2003 | Burdon et al. | 422/186.29 |
| 6,623,860 B2 * | 9/2003 | Hu et al. | 428/411.1 |
| 6,676,835 B2 * | 1/2004 | O'Connor et al. | 422/100 |
| 2001/0048637 A1 | 12/2001 | Weigl et al. | 366/341 |
| 2001/0048900 A1 | 12/2001 | Bardell et al. | 422/100 |
| 2002/0048535 A1 | 4/2002 | Weigl et al. | 422/100 |
| 2002/0076350 A1 | 6/2002 | Weigl et al. | 422/58 |
| 2002/0192701 A1 * | 12/2002 | Adey | 435/6 |
| 2003/0123322 A1 | 7/2003 | Chung et al. | 366/165.1 |

OTHER PUBLICATIONS

Liu, Robin H. et al., "Plastic In–Line Chaotic Micromixer for Biological Applications," *Micro Total Analysis Systems*, J.M. Ramsey and A. van den Berg (eds.), 2001 Kluwer Academic Publishers, The Netherlands, pp. 163–164.

Jacoby, Mitch, *Chemistry Flows Like Clockwork —Flow system used to make simple devices for time–dependent studies*, "Channels & Engineering News," Feb. 24, 2003, p. 5.

Dshmukh, Ajay A. et al., A.P. (2000), "Continuouse Micromixer with Pulsatile Micropumps," Solid–State Sensor and Achuator Workshop, Hilton Head Island, SC, USA, Jun. 4–8, 2000, pp. 73–76.

Martin, P.M. et al., *Laser micromachined and laminated microchannel components for chemical sensors and heat transfer applications*, "Micromachined Devices and Components III," SPIE—The International Society for Optical Engineering, vol. 3224, Bellingham, Washington, USA, pp. 258–265.

Tracey, M.C. et al., "Microfluidic Mixer Employing temporally–Interleaved Liquid Slugs and Parabolic Flow," *Micro Total Analysis Systems*, J.M. Ramsey and A. van den Berg (eds.) 2001 Kluwer Academic Publishers, The Netherlands, pp. 141–142.

Ehrfeld, W. et al., *Potentials and Reallization of Microreactors*, "DECHEMA Monographs," vol. 132, VCH Verlagsgesellschaft, 1996, pp. 1–28.

Johnson, Timothy J. et al., *Rapid Microfluidic Mixing*, "Analytical Chemistry," vol. 74, No. 1, Jan. 1, 2002, pp. 45–51.

Verporte, Elisabeth M.J. et al., "Silicon–based Chemical Microsensors and Microsystems," *Interfacial Design and Chemical Sensing*, American Chemical Society, 1994, Chapter 21, pp. 244–254.

Yang, Xing et al., "A MEMS Thermopneumatic Silicone Membrane Valve," (1998) Sensors and Actuators A: Physical, vol. 64, pp. 101–108.

Schulta, Thomas, "The Development of Pratical Microfluidic–Based Systems for Chemical and Blood Analysis," (1999) in Drug–Discovery Technology for the New Millenium Chapter 13, pp 127–135. Conference proceeding: IBC USA Conferences, Inc.: $4^{th}$ Annual Conference on Microfabrication and Microfluidic Tehcnologies.

Becker, Holger et al., "Silicon as Tool Materials for Polymer Hot Embossing," (1999) Proceedings MEMS'99 Orlando, 228–231.

Jeon, Noo Li et al., "Large–Area Patterning by Vacuum–Assisted Micromolding," (1999) Adv. Mater.. 11, No. 11:946–950.

Jackman, Rebecca J., et al., "Electrochemistry and soft Lithograph: A route 3–D microstructures", (May 1999) Cehmtech 18–30.

Folch, A., et al., "Molding of Deep Polydimethylsiloxane Microstructures for Microfluidics and Biological Applications"(Feb. 1999) Journal of Biomechanical Engineering 121:28–34.

Duffy, David C., et al., "Rapid Prototyping of Microfluidic Systems in Poly(dimethylsiloxane)", (Dec. 1998) Analytical Chemistry 70:4974–4984.

Grzybowski, B, et al., "Generation of Micrometer–Szied Patterns for Miccranalytical Application Using a Laser Driect–Write Method and Microcontant Printing", (Nov 1998) Anaylitical Chemistry 70:4645–4652.

Gonzalez, C., et al., "Fluidic internconects for modular assembly of Chemical Microsystems", (Jan 1998), Sensors and Actuators B 49:40–45.

Qin, Dong, et al., "Microfabrication, and Microsystems", (1998) Topics in Current Chemistry 194:1–19.

Fuhr, G., et al., "Biological Application of Microstructures", (1998) Topics in Current Chemistry 194:83–116.

Cordova, Emilio, et al., "Noncovalent Polycationnic Coatings for Capillaries in Capillary Electrophoresis of Proteins" (Apr. 1997) Analytical Chemistry 69:1370–1379.

McCormick, Rnady M., et al., "Microchannel Electrochannel Electrophoretic Separations of DNA in Injection–Molded Plastic Substrates"(Dec. 1997) Analytical Chemistry 69:2626–2630.

Martynova, Larisa et al., "Fabrication of Plastics Microfluid Channels by Imprinting Methods" (1997) Anal. Chem. 69:4783–4789.

Kovacs, Gregory T.A. et al., "Silicon Micromachining Sensors to Systems" (Jul. 1996) Analytical Chemistry News & Features 407A–412A.

Shoji, Shuchi, et al., "Microflow Devices and Systems" (Oct. 1994). J. Micromech. Microeng. 4:157–171.

Schomburg, W.K., et al., "Microfluidic Components in LIGA Technique" (Feb. 1994) J. Micromech.Microeng. 4:186–191.

Verport, Elisabeth M.J., et al., "Three–Dimensional Micro Flow Manifolds for Miniaturized Chemical Analysis Systems"(Oct. 1994) J. Micromech. Microeng. 4:246–256.

Groisman, et al., *Microfluidic Memory and Control Devices,* "Science Magazine," vol. 300, May 9, 2003, pp. 955–958.

Ehrfeld, et al., *Injection of Many Small Substreams of One Component into a Main Stream of Another Component,* "Microreactors—New Technology for Modern Chemistry," Vch. Verlagsgesellschaft Mbh; $1^{st}$ edition, Jun. 15, 2000, pp. 53–55.

Branebjerg, Jens, et al., "Fast Mixing by Lamination," Proc. Micro Electro Mechanical Systems Workshop, pp. 441–446, IEEE (1996).

Miyake, Ryo et al., "Micro Mixer with Fast Diffusion," Proc. Micro Electro Mechanical Systems Workshop, pp. 248–253, IEEE (1993).

Mensinger, H., et al., "Microreactor With Integrated Static Mixer and Analysis System," Micro Total Analysis Systems, pp. 237–240, Kluwer, The Netherlands (1995).

Larsen, Ulrik D., et al.. "Fast Mixing by Parallel Multilayer Lamination," Analytical Methods & Instrumentation, Proc. $2^{nd}$ International Symposium Miniaturized Total Analysis Systems, µTAS–96, pp. 228–230 (1996).

Bertsch, Arnaud, et al., "Static Micromixers Based on Large–Scale Industrial Mixer Geometry," Lab On A Chip, vol. 1, pp. 56–60, 2001.

Voldman, Joel, et al., "An Integrated Liquid Mixer/Valve," Journal of Microelectromechanical Sys., vol. 9, No. 3, Sept. 2000.

Weigl, Bernhard H., et al., "Passive Microfluidics—Ultra low–cost plastic disposable lab–on–a–chip," µTAS 2000, Twente, the Netherlands, May 14–18, 2000.

Merkel, Tobias, et al., "A NEw Technology for Fluidic Microsystems Based on PCB Technology," Sensors and Actuators 77 A:Physical, pp. 98–105, 1999.

McNeely, Michael R., et al., "Hydrophobic Microfluidics," SPIE Microfluidic Devices & Systems II, vol. 3877, Sept. 1999.

Ehrfeld, Wolfgang et al., "Characterization of Mixing in Micromixers by a Test Reaction: Single Mixing Units and Mixer Arrays," Ind. Eng. Chem. Res. 1999, 38 1075–1082, Jan. 23, 1999.

Bökenkamp, Dirk, et al., "Microfabricated Silicon Mixers for Submillisecond Quench–Flow Analysis," Anal. Chem. 70, pp. 232–236, 1998.

Shoji, Shuichi, "Fluids for Sensor Systems,"Topics in Current Chemistry, vol. 194, 1998.

Knight, James B., et al., "Hydrodynamic Focusing on a Silicon Chip: Mixing Nanoliters in Microseconds," Physical Review Letters, vol. 80, No. 17, Apr. 27, 1998.

Desai, Amish et al., Microfludic Sub–millisecond Mixers For The Study of Chemical Reaction Kinetics, Tranducers 97 (1997 Int'l Conf. On Solid–State Sensors and Actuators), vol. 1 pp. 167–170, Jun. 16–19, 1997.

Svasek,P., et al., "Dry Film Resist Based Fluid Handling Components for µTAS" Institute für Allgemeine Elektrotechnik und Elektronik, Technische Universität Wien, (Undated).

* cited by examiner

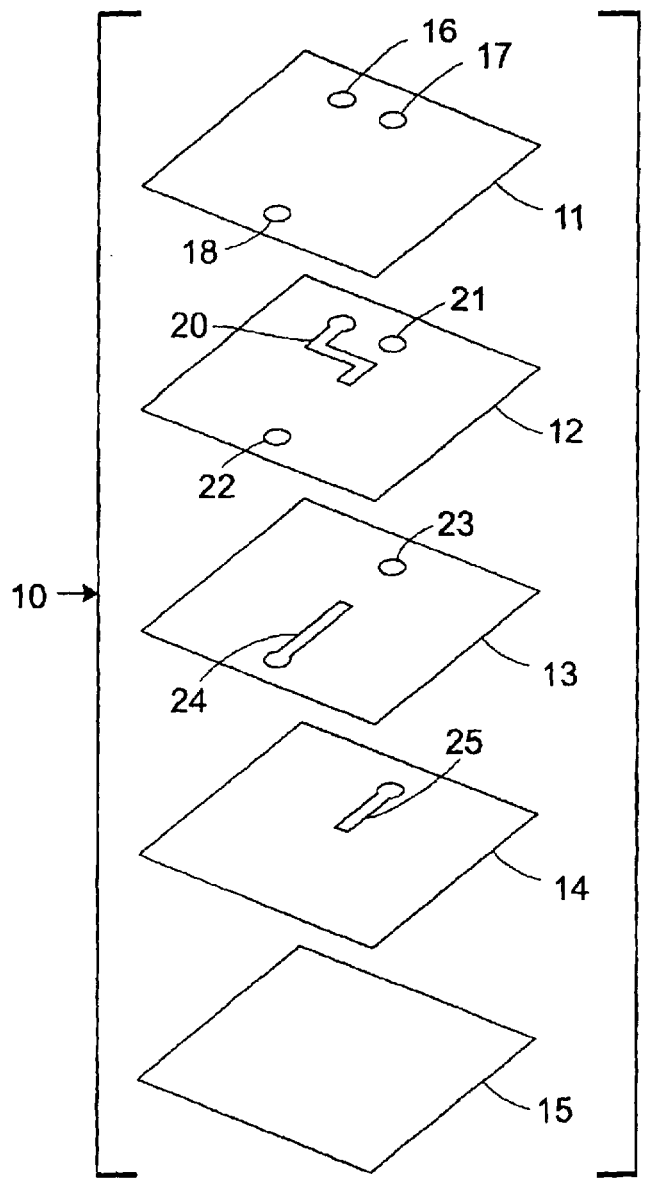
FIG._1A
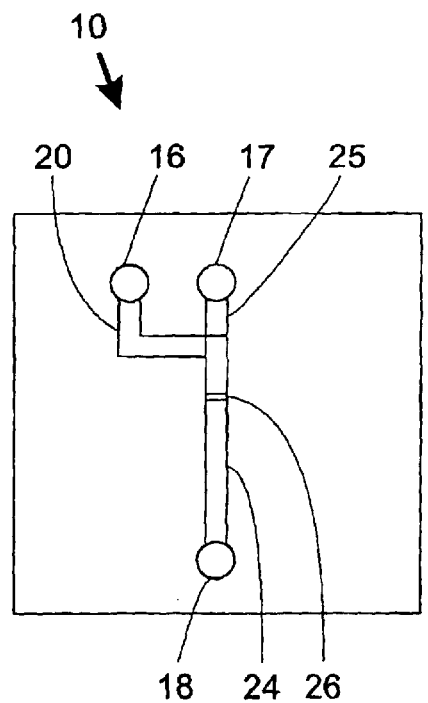
FIG._1B

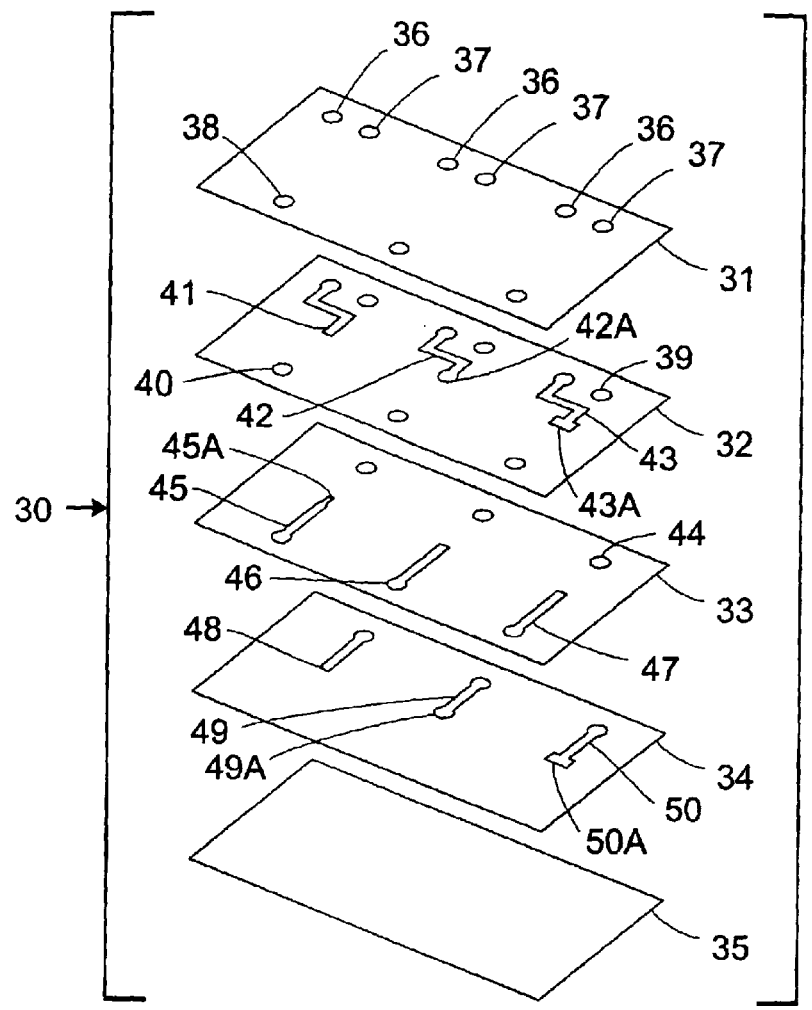
FIG._2A
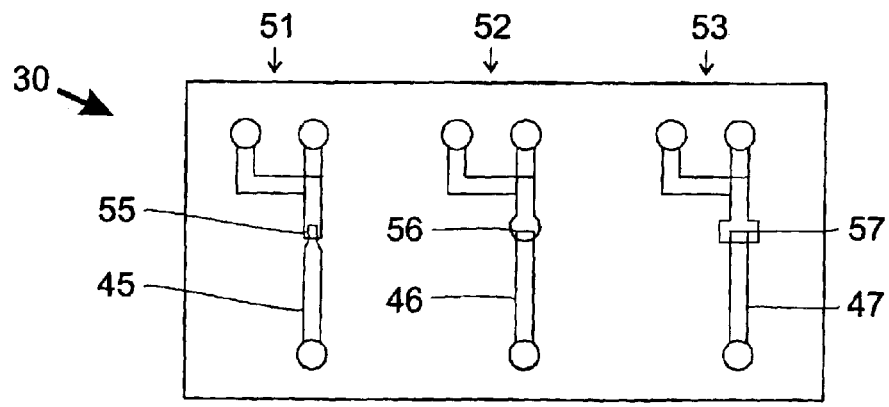
FIG._2B

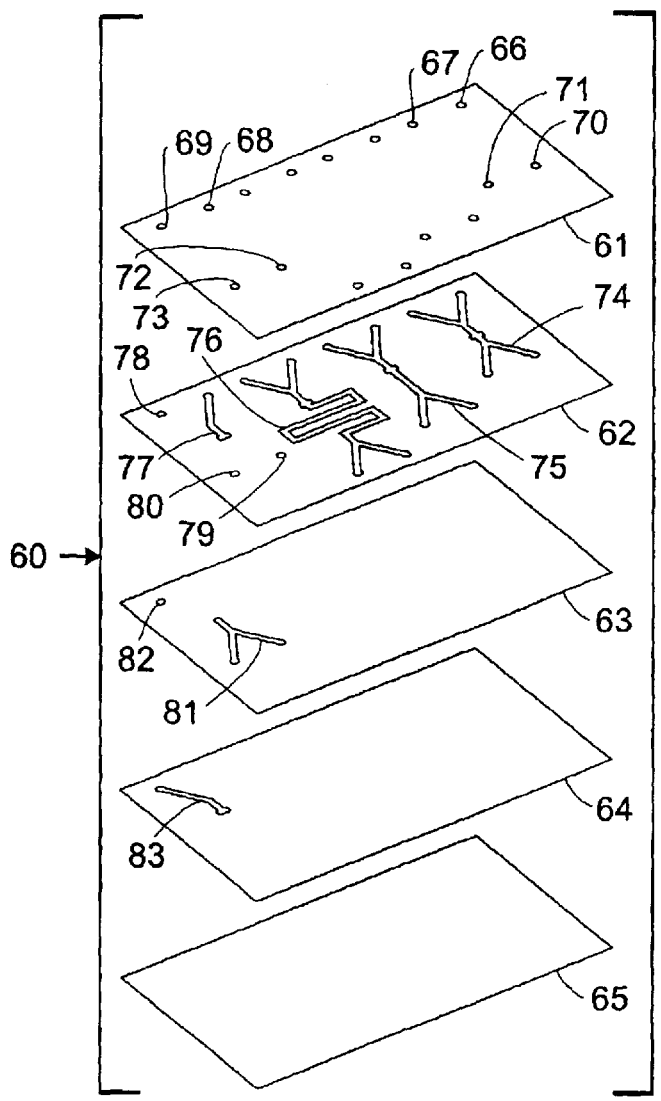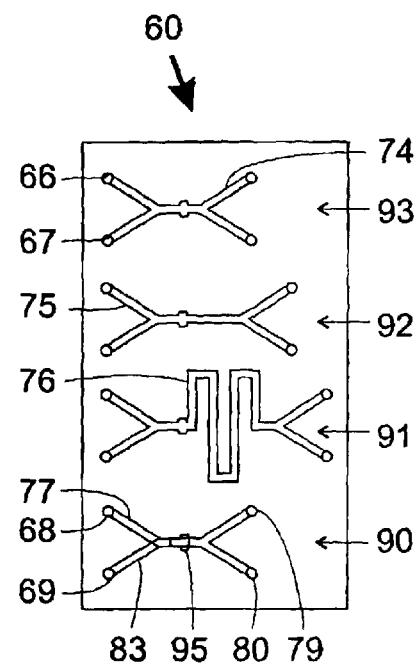
FIG._3A
FIG._3B

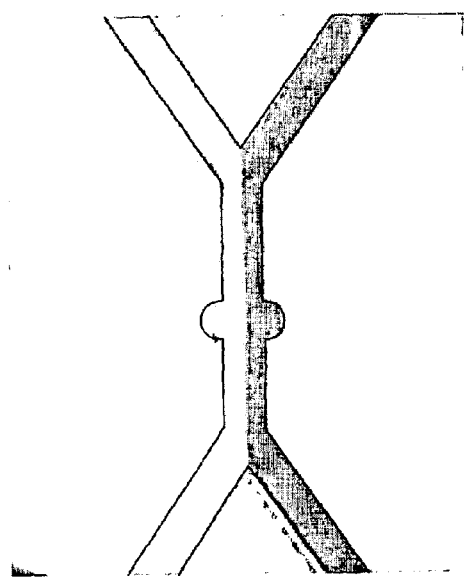
FIG._ 4A
(PRIOR ART)
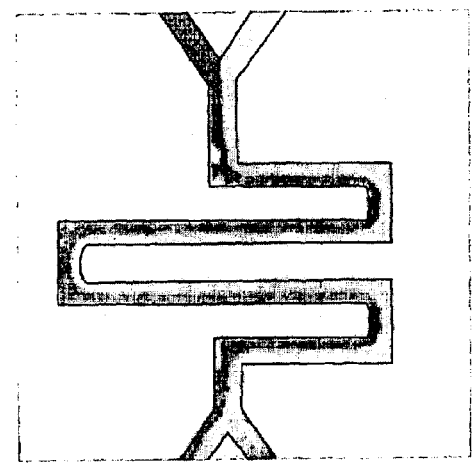
FIG._ 4B
(PRIOR ART)
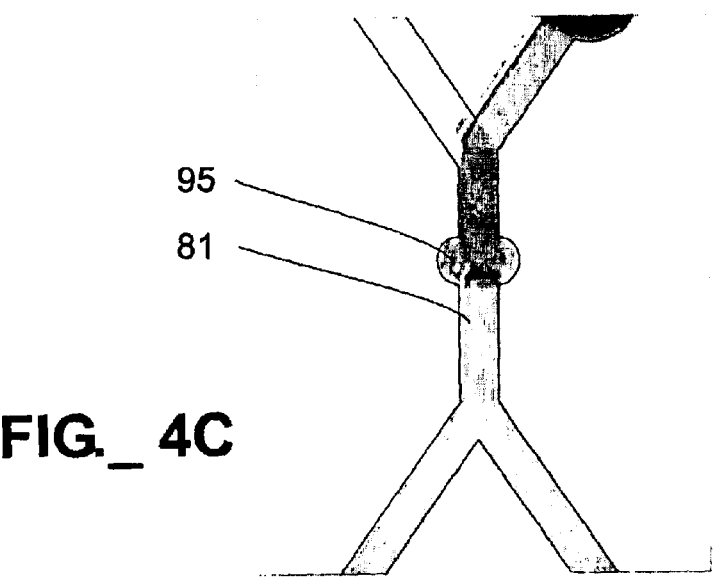
FIG._ 4C

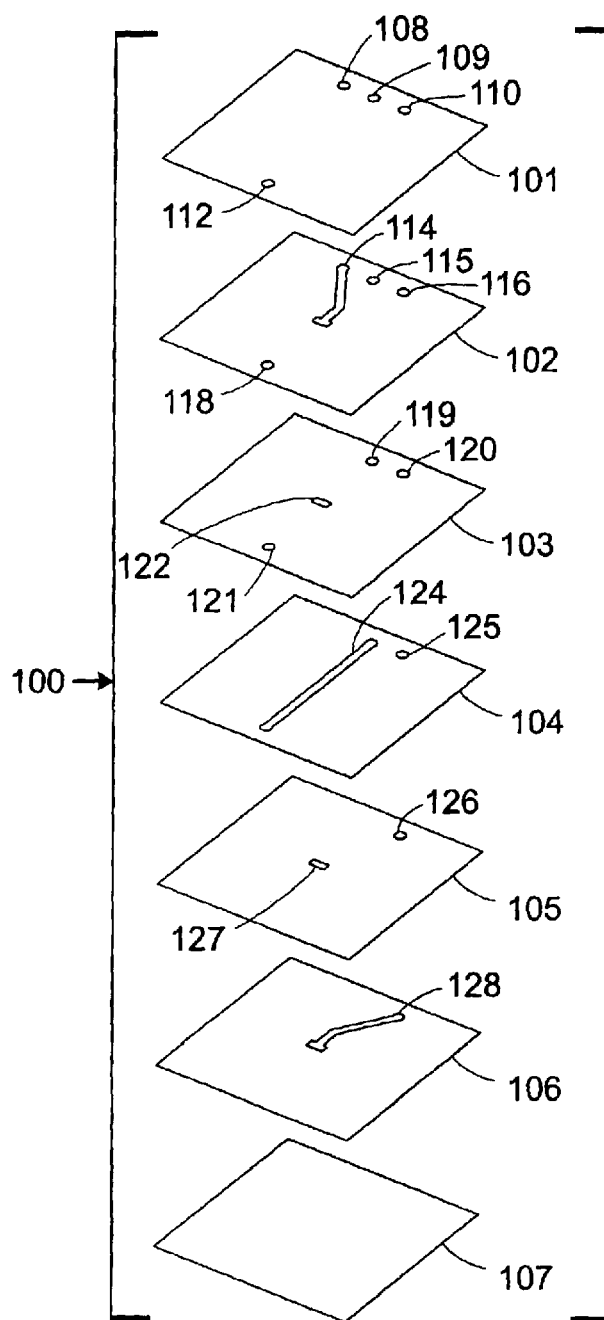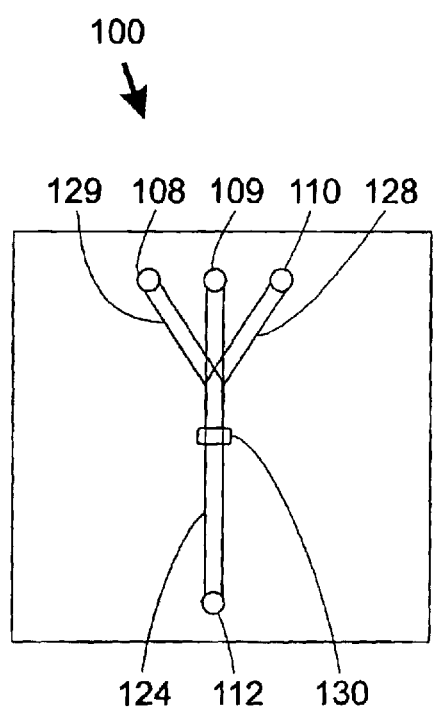
FIG._5A
FIG._5B

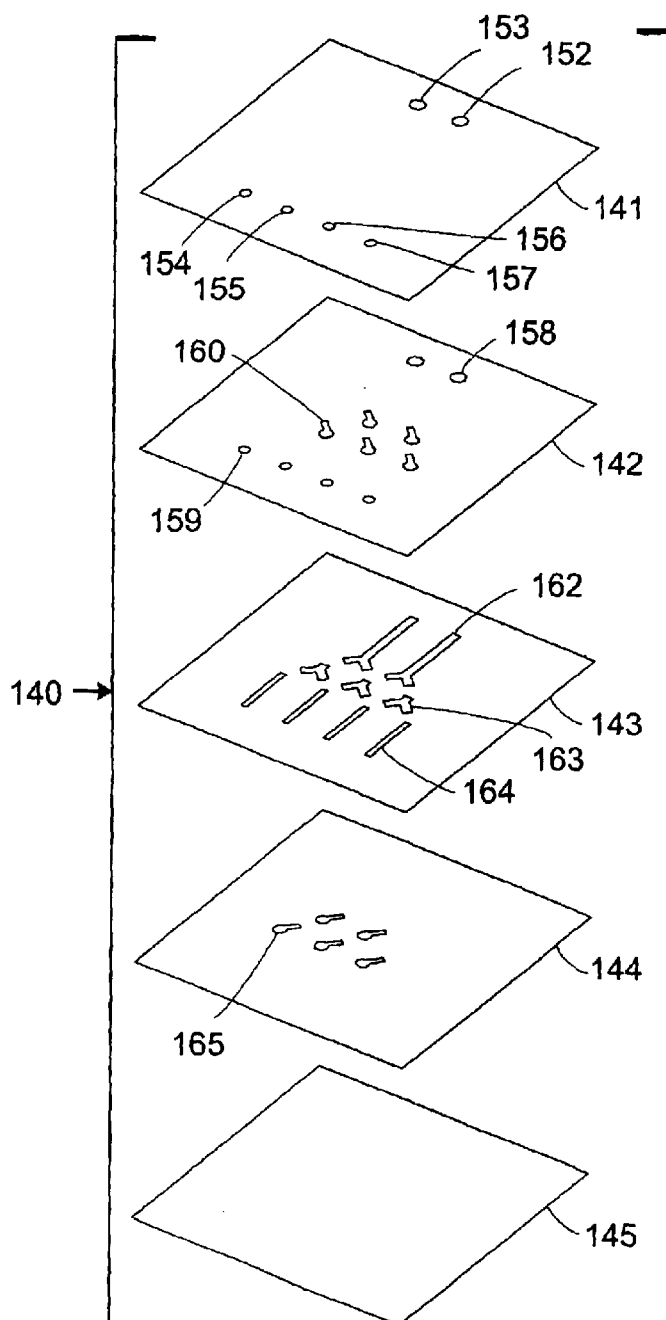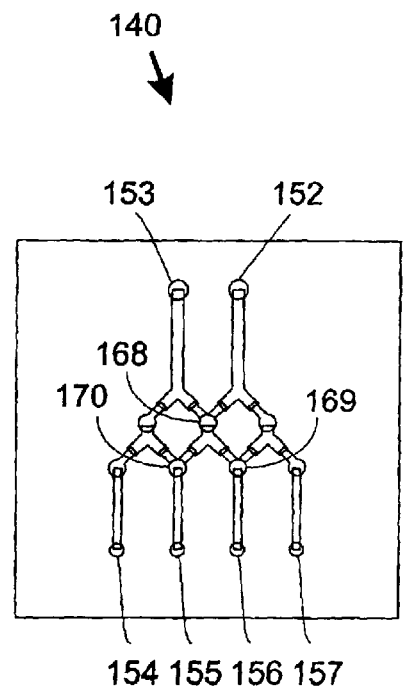
FIG._6A
FIG._6B

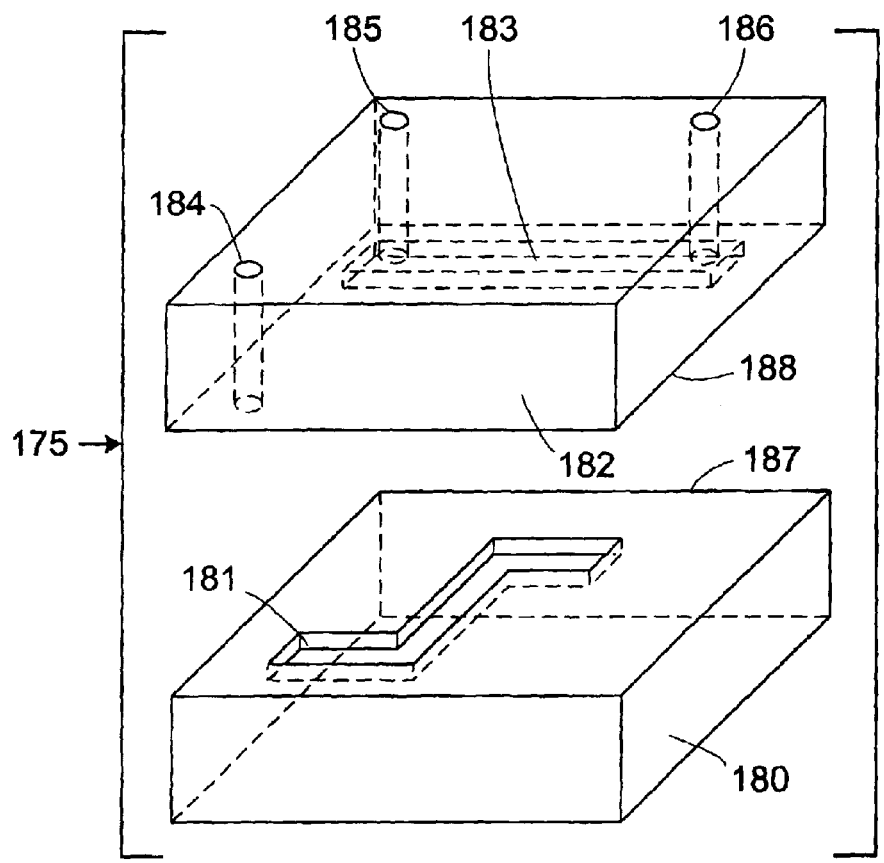
FIG._7A
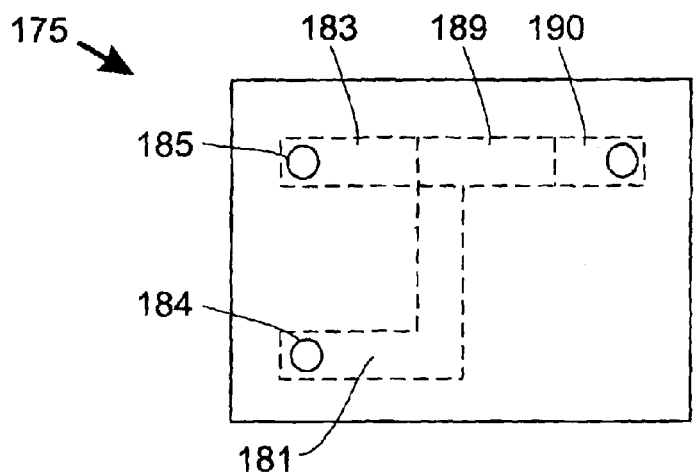
FIG._7B

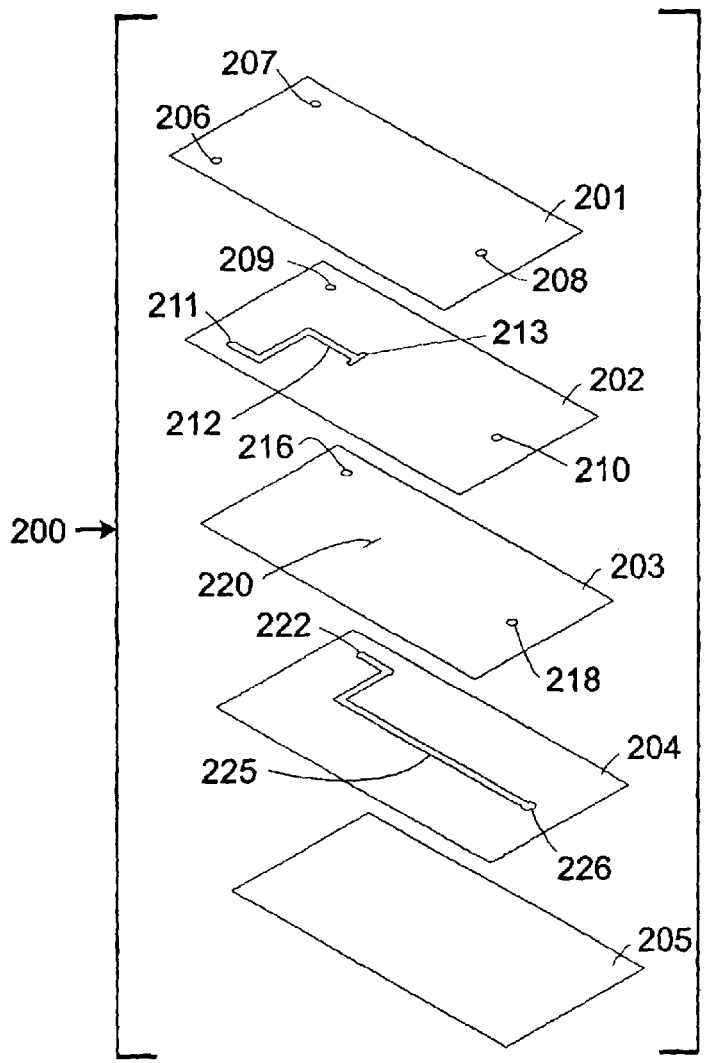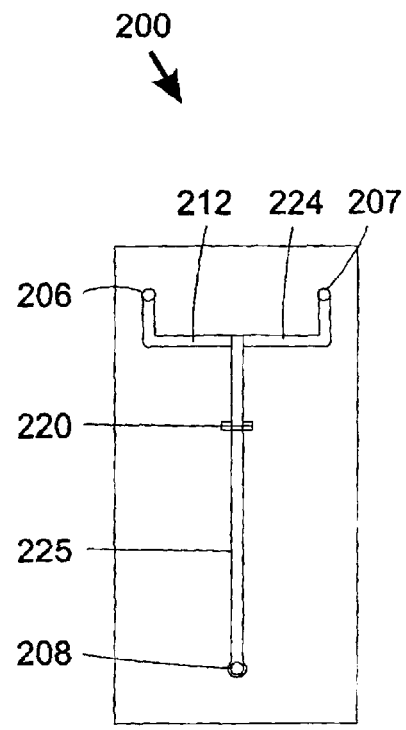
FIG._8A
FIG._8B

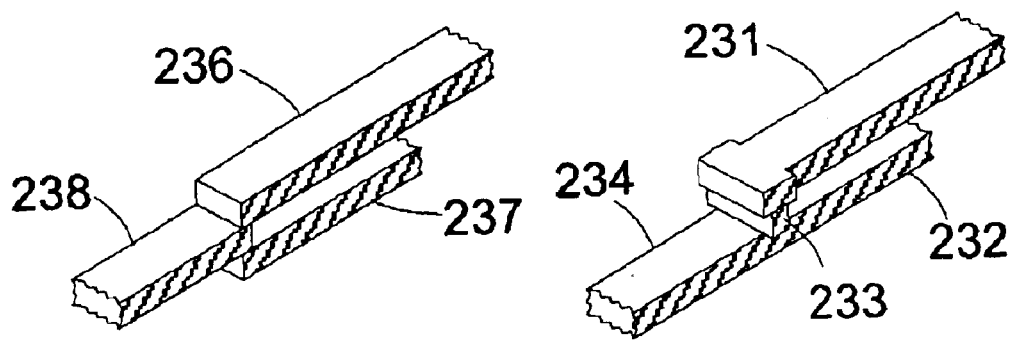
FIG._9A  FIG._9B

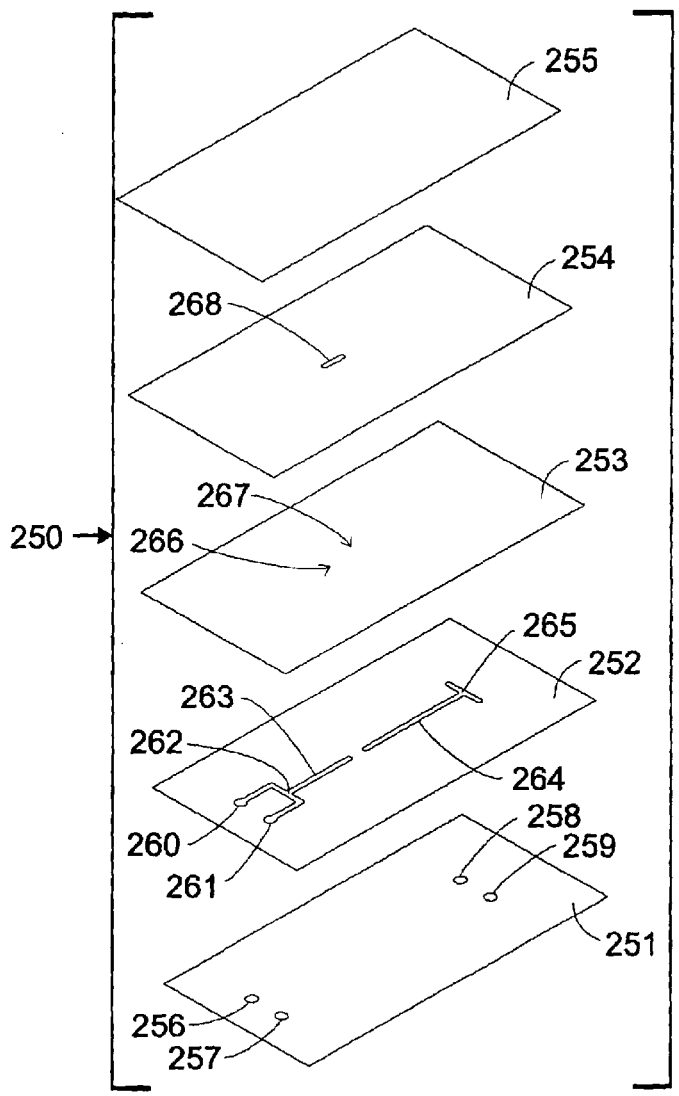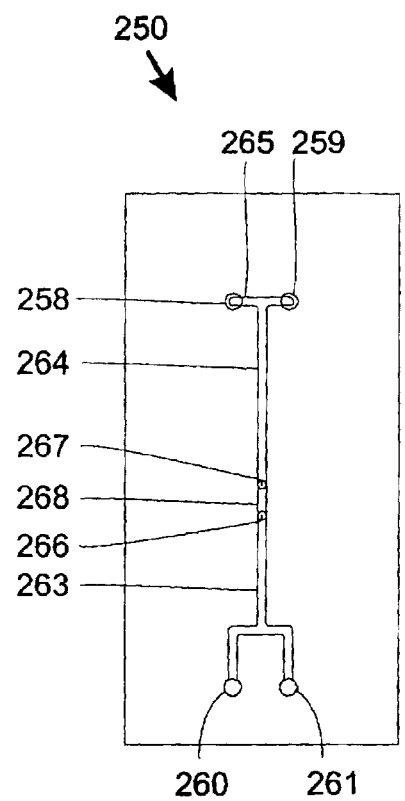
FIG._10A
FIG._10B

FIG._10C 
FIG._10D 

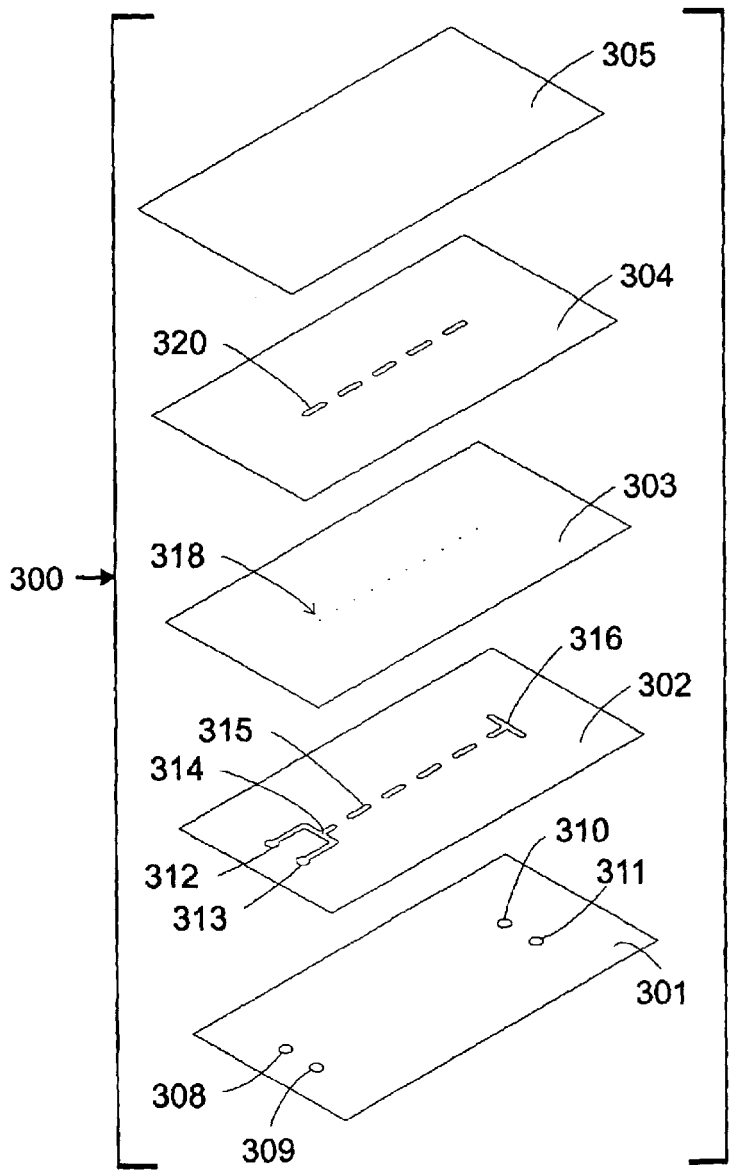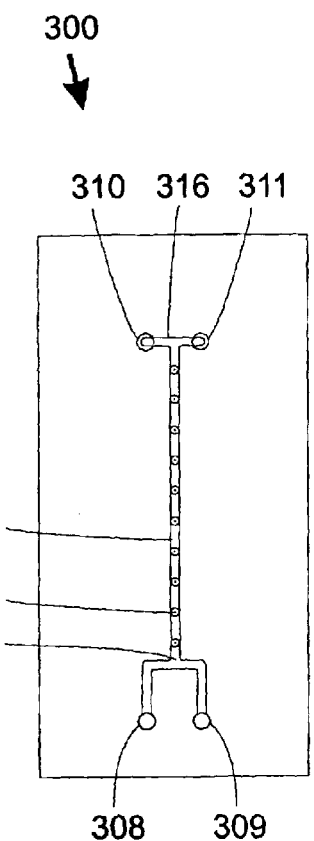
FIG._11A
FIG._11B

FIG._11C 
FIG._11D 
FIG._11E 

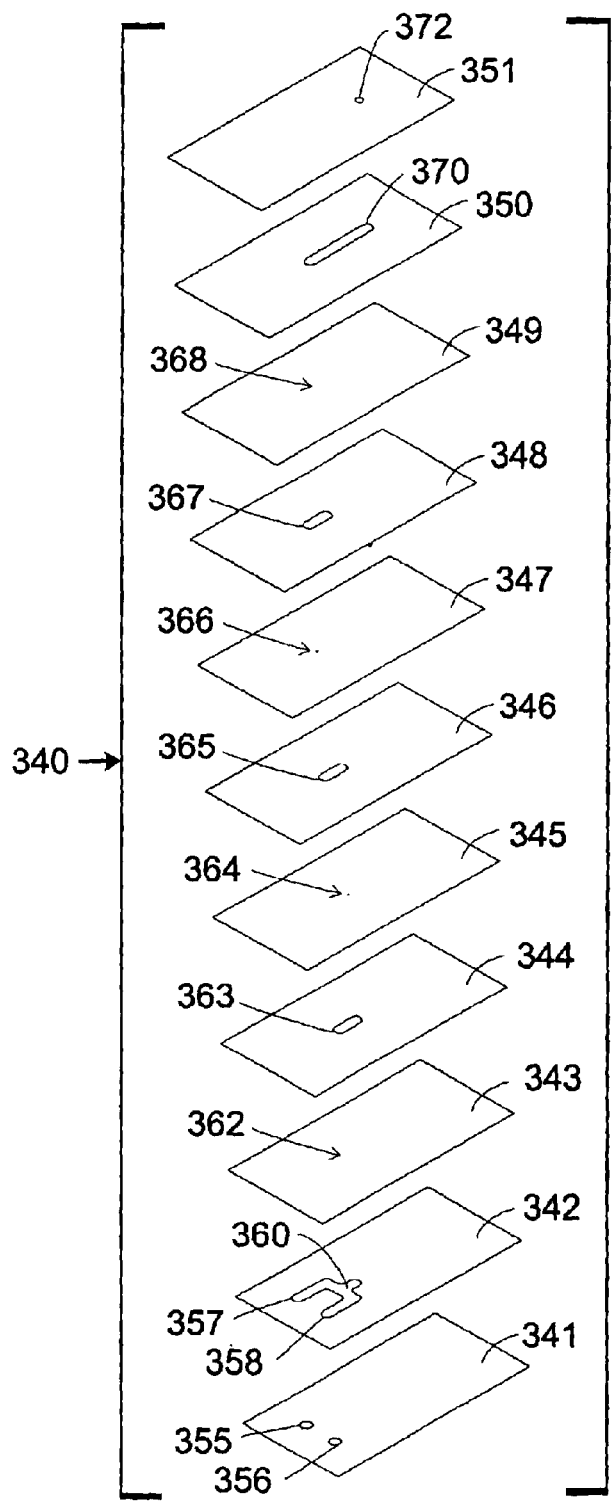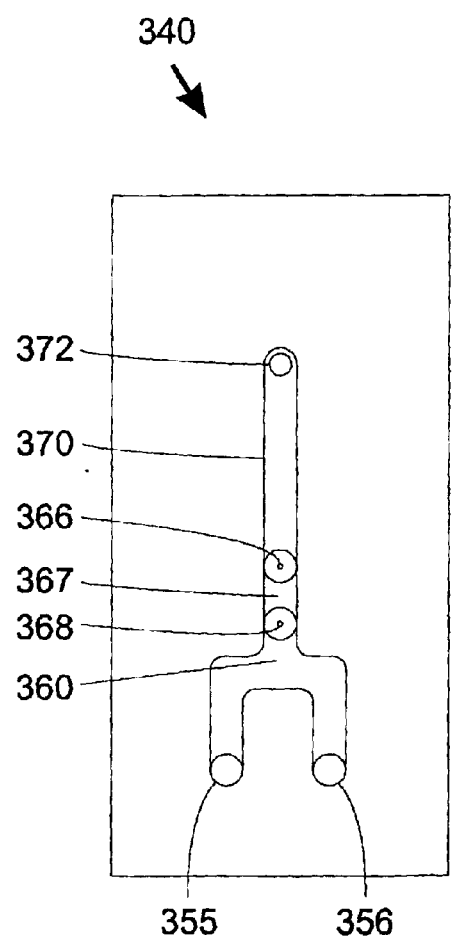
FIG._12A
FIG._12B

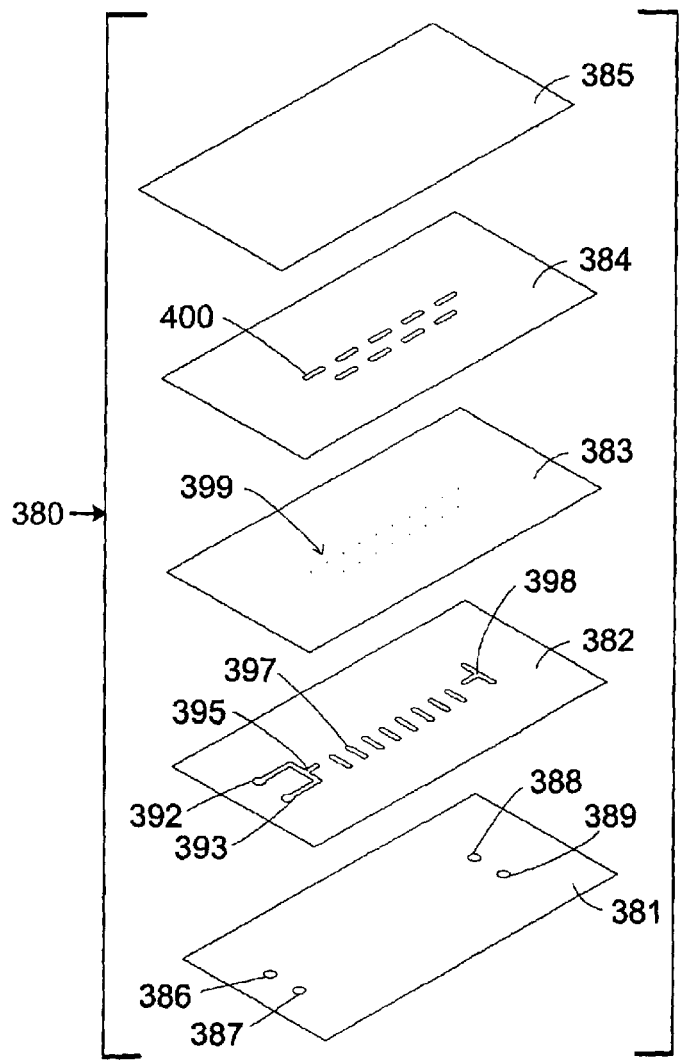
FIG._13A
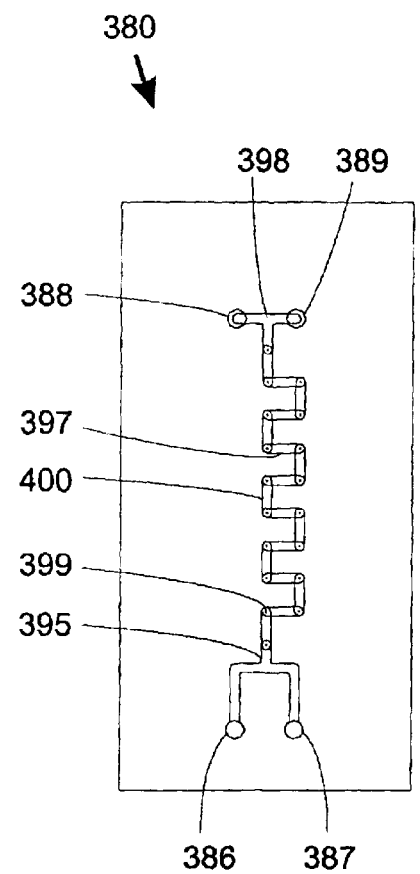
FIG._13B

FIG._13C
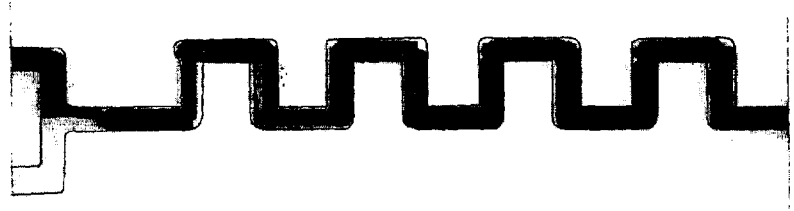
FIG._13D
FIG._13E

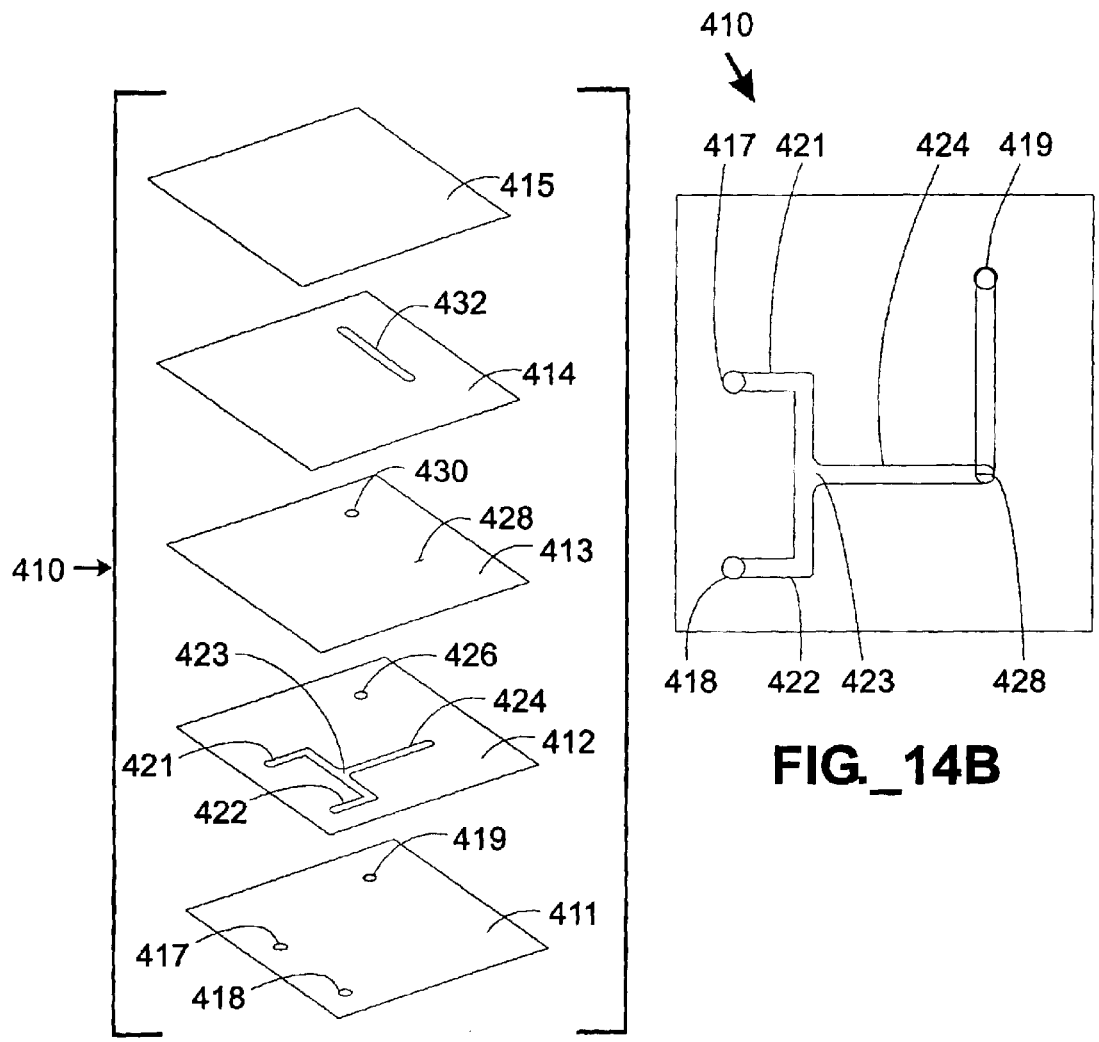
FIG._14A
FIG._14B

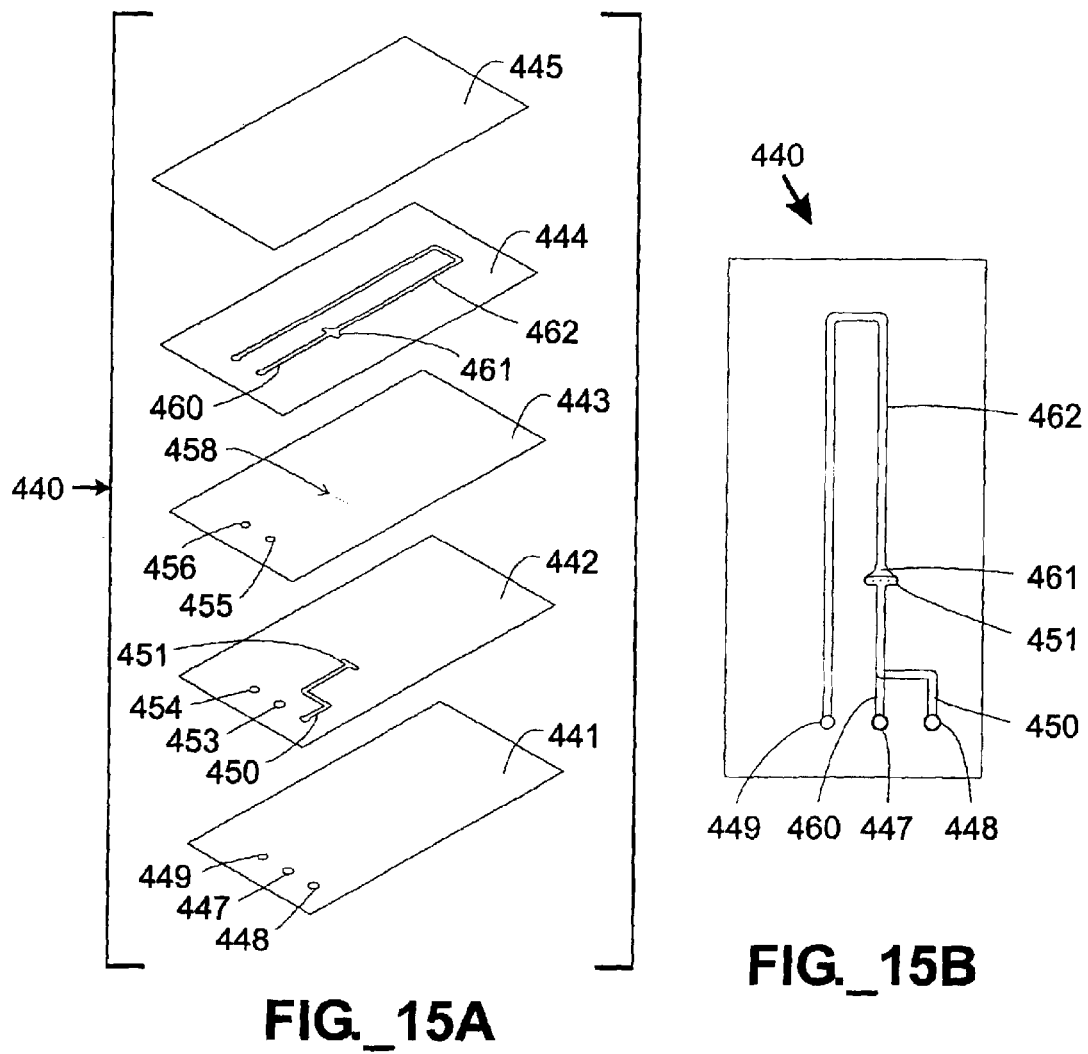
FIG._15A
FIG._15B

FIG._15C
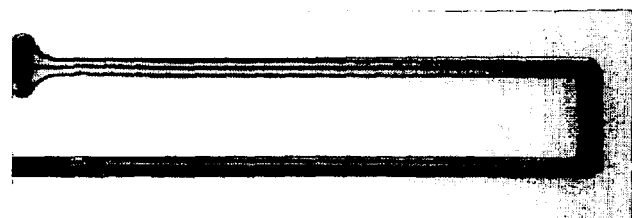
FIG._15D
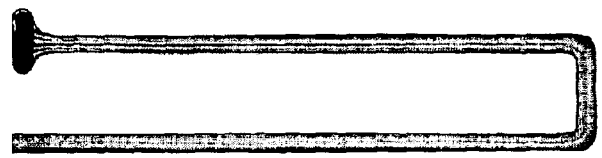

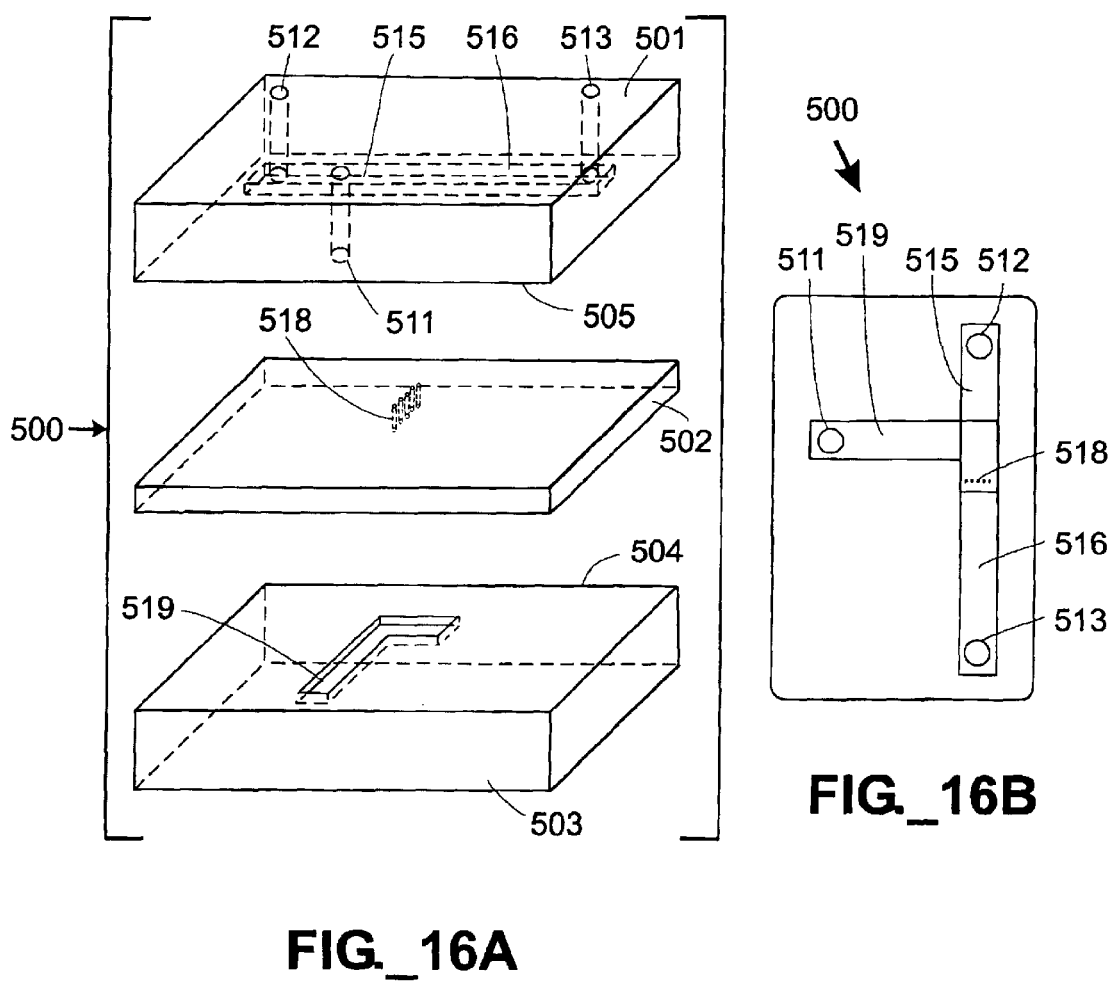
FIG._16B
FIG._16A

MULTI-STREAM MICROFLUDIC MIXERS

STATEMENT OF RELATED APPLICATION(S)

This application is filed as a continuation-in-part of U.S. patent application Ser. No. 09/632,681, filed Aug. 7, 2000, now abandoned. This application also claims benefit of co-pending U.S. Provisional Patent Application Ser. No. 60/296,882, filed Jun. 7, 2001.

FIELD OF THE INVENTION

The present invention relates to manipulation, and more particularly, mixing, of fluids in microfluidic systems.

BACKGROUND OF THE INVENTION

There has been a growing interest in the application of microfluidic systems to a variety of technical areas, including such diverse fields as biochemical analysis, medical diagnostics, chemical synthesis, and environmental monitoring. For example, use of microfluidic systems for acquiring chemical and biological information presents certain advantages. In particular, microfluidic systems permit complicated biochemical reactions and processes to be carried out using very small volumes of fluid. In addition to minimizing sample volume, microfluidic systems increase the response time of reactions and reduce reagent consumption. Furthermore, when conducted in microfluidic volumes, a large number of complicated biochemical reactions and/or processes may be carried out in a small area, such as in a single integrated device. Examples of desirable applications for microfluidic technology include analytical chemistry; chemical and biological synthesis, DNA amplification; and screening of chemical and biological agents for activity, among others.

Traditional methods for constructing microfluidic devices have used surface micromachining techniques borrowed from the silicon fabrication industry. According to these techniques, microfluidic devices have been constructed in a planar fashion, typically covered with a glass or other cover material to enclose fluid channels. Representative devices are described, for example, in some early work by Manz, et al. (Trends in Anal. Chem. (1990) 10(5): 144–149; Advances in Chromatography (1993) 33: 1–66). These publications describe microfluidic devices constructed using photolithography to pattern channels on silicon or glass substrates, followed by application of surface etching techniques to remove material from a substrate to form channels. Thereafter, a cover plate is typically to the top of an etched substrate to enclose the channels and contain a flowing fluid.

More recently, a number of methods have been developed that allow microfluidic devices to be constructed from plastic, silicone or other polymeric materials. Fabrication methods include micromolding of plastics or silicone using surface-etched silicon as the mold material (see, e.g., Duffy et al., Anal. Chem. (1998) 70: 4974–4984; McCormick et al., Anal. Chem. (1997) 69: 2626–2630); injection-molding; and micromolding using a LIGA technique (see, e.g., Schomburg et al., Journal of Micromechanical Microengineering (1994) 4: 186–191), as developed at the Karolsruhe Nuclear Research Center in Germany and commercialized by MicroParts (Dortmund, Germany). LIGA and hot-embossing techniques have also been demonstrated by Jenoptik (Jena, Germany). Imprinting methods in polymethylmethacrylate (PMMA) have also been described (see, e.g., Martynova et al., Anal. Chem. (1997) 69: 4783–4789). These various techniques are typically used to fashion planar (i.e., two dimensional, or 2-D) structures that require some sort of cover to enclose microfluidic channels. Additionally, these techniques do not lend themselves to rapid prototyping and manufacturing flexibility. Moreover, the tool-up costs for such techniques are often quite high and can be cost-prohibitive A more recent method for constructing microfluidic devices uses a KrF laser to perform bulk laser ablation in fluorocarbons that have been compounded with carbon black to cause the fluorocarbon to be absorptive of the KrF laser (see, e.g., McNeely et a., "Hydrophobic Microfluidics," SPIE Microfluidic Devices & Systems I/I, Vol. 3877 (1999)). This method is reported to reduce prototyping time; however, the addition of carbon black renders the material optically impure and presents potential chemical compatibility issues. Additionally, the reference is directed only to planar structures.

When working with fluids in conventional macroscopic volumes, achieving effective mixing between two or more fluid streams is a relatively straightforward task. Various conventional strategies may be employed to induce turbulent regions that cause fluid streams to mix rapidly. For example, active stirring or mixing elements (e.g., mechanically or magnetically driven) may be employed. Alternatively, special geometries may be employed in flow channels to promote mixing without the use of moving elements. One common example of the use of special geometries includes the addition of baffles to deflect flowing fluid streams and thereby promote turbulence.

Applying conventional mixing strategies to microfluidic volumes is generally ineffective, impractical, or both. To begin with, microfluidic systems are characterized by extremely high surface-to-volume ratios and correspondingly low Reynolds numbers (less than 2000) for most achievable fluid flow rates. At such low Reynolds numbers, fluid flow within most microfluidic systems is squarely within the laminar regime, and mixing between fluid streams is motivated primarily by the phenomenon of diffusion—typically a relatively slow process. In the laminar regime, using conventional geometric modifications such as baffles is generally ineffective for promoting mixing. Moreover, the task of integrating moveable stirring elements and/or their drive means in microfluidic devices would be prohibitively difficult using conventional means due to volumetric and/or cost constraints, in addition to concerns regarding their complexity and reliability. In light of these limitations, it would be desirable to provide a microfluidic mixer that could rapidly mix fluid streams without moving parts, in a minimal space, and at a very low construction cost. An ideal fluid mixer would further be characterized by minimal dead volume to facilitate mixing of extremely small fluid volumes.

Passive microfluidic mixing devices have been constructed in substantially planar microfluidic systems where the fluids are allowed to mix through diffusion (e.g., Bokenkamp, et al., Analytical Chemistry (1998) 70(2): 232–236. In these systems, fluid mixing occurs at the interface of the fluids, which is commonly small relative to the overall volume of the fluids. Thus, mixing occurs in such devices very slowly.

Another passive microfluidic mixer has been proposed by Erbacher and Manz in WIPO International Application Number PCT/EP96/02425 (Publication Number WO 97/00125), published Jan. 3, 1997. There, a flow cell for mixing of at least two flowable substances includes multiple fluid distribution troughs (one for each substance) leading to a fan-like converging planar flow bed, all disposed between fluid inlets and an outlet. One limitation of the disclosed mixing apparatus is that its components (e.g., supply channels, distribution troughs, and flow bed) are fabricated by conventional surface micromachining techniques such as those used for structuring semiconductor materials and lithographic-galvanic LIGA process, with their attendant drawbacks mentioned above. A further limitation of the disclosed mixing apparatus are that its components consume a relatively large volume, thus limiting the ability to place many such mixers on a single device and providing a large potential dead volume.

A so-called "microlaminar mixer" is provided in U.S. Pat. No. 6,264,900 to Schubert, et al. There, an improved nozzle includes a microfabricated guide that supplies multiple distinct fluid layers to an external collecting tank or chamber. Various reactive fluid streams are kept spatially separated until they emerge from the guide, specifically to prevent the starting components from coming into contact with one another within the device. One limitation of the disclosed nozzle-type system is that its "guide" component is fabricated with conventional surface micromachining techniques with their attendant drawbacks. A further limitation of this nozzle-type system is that it would be highly impractical, if not impossible, to integrate such components into a single microfluidic device for further manipulation of the resulting fluid following the mixing step.

Alternative mixing methods have been developed based on electrokinetic flow. Devices utilizing such methods are complicated, requiring electrical contacts within the system. Additionally these systems only work with charged fluids, or fluids containing electrolytes. Finally, these systems require voltages that are sufficiently high to cause electrolysis of water, thus causing problems with bubble formation is a problem and collecting samples without destroying them.

In light of the limitations of conventional microfluidic mixers, there exists a need for robust mixers capable of rapidly and thoroughly mixing a wide variety of fluids within a minimal volume in a microfluidic environment. Such mixer designs would preferably be amenable to rapid, low cost fabrication in both low and high volumes, would be suitable for prototyping and large-scale manufacturing, and would permit further processing of fluids downstream of any mixing region(s).

SUMMARY OF THE INVENTION

As is further discussed in the detailed description, microfluidic mixing devices according to different embodiments may be constructed in various different materials and in various geometries or layouts. Various embodiments are directed to passively mixing at least two or more than two different fluid streams.

In a first separate aspect of the invention, a multi-layer passive microfluidic mixing device includes a first microfluidic channel defined through a first stencil layer, a second microfluidic channel defined through a second stencil layer, and an overlap region in fluid communication with both channels to promote mixing between multiple fluid streams. Such a device may be constructed in various different geometries, either with or without an intermediate spacer layer.

In another separate aspect of the invention, a multi-layer microfluidic mixing device includes a first microfluidic channel for transporting a first fluid stream, a second microfluidic channel for transporting a second fluid stream, a microfluidic outlet channel, and an overlap region for contacting the first fluid stream with the second fluid stream in the outlet channel to promote mixing. The first channel is defined through the entire thickness of a first stencil layer and the second channel is defined through the entire thickness of a second stencil layer. The device may be constructed in various different geometries, and an intermediate spacer layer may be optionally included.

In another separate aspect of the invention, a microfluidic device for mixing multiple fluid streams includes multiple inlet channels that merge into a junction channel and multiple contraction/expansion regions in fluid communication with the junction channel. The junction channel is defined in a first device layer. Each contraction/expansion region includes a small aperture or opening defined in a second device layer and a microfluidic expansion channel defined in either the first device layer or a third device layer.

In yet another separate aspect of the invention, a multilayer microfluidic mixing device includes multiple inlet channels that merge into a junction channel defined in a first device layer, a slit defined in a second device layer, and a microfluidic outlet channel defined in a third device layer. The slit is in fluid communication with both the junction channel and the outlet channel, and the slit is aligned lengthwise in a direction substantially parallel to the junction channel.

In still another separate aspect of the invention, a microfluidic mixing device includes a first microfluidic channel defined in a first device layer, a second microfluidic channel defined in a second device layer, and a slit defined in a third device layer, the slit permitting fluid communication between the first channel and the second channel.

In another separate aspect of the invention, a microfluidic mixing device includes a first microfluidic channel defined in a first device layer, a second microfluidic channel defined in a second device layer, and a third device layer positioned between the first and second device layers. The third layer defines multiple apertures in fluid communication with the first channel and the second channel.

In yet another separate aspect of the invention, a microfluidic mixing device for mixing different fluids in multiple proportions includes a first microfluidic channel having a forked region for splitting a first fluid stream into multiple sub-streams and a second microfluidic channel have a forked region for splitting a second fluid stream into multiple sub-streams. The mixing device further includes multiple overlap regions each contacting a sub-stream of the first fluid with a sub-stream of the second fluid to promote fluidic mixing.

In a further aspect of the invention, any of the foregoing separate aspects may be combined for additional advantage.

These and other aspects and objects of the invention will be apparent to one skilled in the art upon review of the following detailed disclosure, drawings, and claims.

BRIEF DESCRIPTION OF THE DRAWINGS

FIG. 1A is an exploded perspective view of a microfluidic mixing device capable of mixing two fluids, the device constructed in five layers and having a channel overlap region. FIG. 1B is a top view of the assembled device of FIG. 1A.

FIG. 2A is an exploded perspective view of a microfluidic mixing device constructed in five layers, the device having three separate mixing regions each demonstrating different channel overlap geometries. FIG. 2B is a top view of the assembled device of FIG. 2A.

FIG. 3A is an exploded perspective view of a microfluidic mixing device constructed in five layers, the device having four distinct mixing regions capable of mixing two fluids each, with each mixing region followed by a splitting region. FIG. 3B is a top view of the assembled device of FIG. 3A.

FIG. 4A is a top view photograph of a microfluidic mixing device with traced channel borderlines according to a first prior art design that promotes interfacial contact between two side-by-side fluids in a straight channel, wherein only minimal mixing occurs between the two fluids before the aggregate is split into two separate streams. FIG. 4B is a top view photograph of a microfluidic mixing device with traced channel borderlines according to a second prior art design that promotes interfacial contact between two side-by-side fluids in a channel with several turns, wherein incomplete mixing occurs between the two fluids before the aggregate is split into two separate streams. FIG. 4C is a top view photograph of a microfluidic mixing device with traced channel borderlines according to the present invention, demonstrating rapid and complete mixing between two fluids before the aggregate is split into separate streams.

FIG. 5A is an exploded perspective view of a microfluidic mixing device capable of mixing three fluids, the device constructed in six layers. FIG. 5B is a top view of the assembled device of FIG. 5A.

FIG. 6A is an exploded perspective view of a microfluidic mixing device constructed in five layers, the device being capable of simultaneously mixing two fluid input streams in different proportions to yield four output streams. FIG. 6B is a top view of the assembled device of FIG. 6A.

FIG. 7A is an exploded perspective view of a microfluidic mixing device fabricated in two portions using conventional surface micromachining techniques, the device being capable of mixing two fluids. FIG. 7B is a top view of the assembled device of FIG. 7A.

FIG. 8A is an exploded perspective view of a microfluidic mixing device for mixing two fluid streams, the device constructed in five layers and having a narrow slit through which one fluid is introduced to the other. FIG. 8B is a top view of the assembled device of FIG. 8A.

FIG. 9A is a perspective view schematic of portions of two fluid inlet streams and one fluid outlet stream adjacent to a fluid contact region in a microfluidic mixing device, with each inlet stream disposed in a different device layer from the outlet stream. FIG. 9B is a perspective view schematic of two fluid inlet streams and one fluid outlet stream adjacent to a fluid contact region in a microfluidic mixing device, wherein the first inlet stream is disposed in the same device layer as the outlet stream, and the second inlet stream contacts the first inlet stream through a slit.

FIG. 10A is an exploded perspective view of a microfluidic mixing device constructed in five layers and capable of mixing two fluids, the device having two through-layer contraction/expansion regions disposed in-line with straight inlet and outlet channels. FIG. 10B is a top view of the assembled device of FIG. 10A. FIG. 10C is a top view photograph of the microfluidic mixing device of FIGS. 10A–10B with traced channel borderlines, showing the mixing pattern for mixing between two fluids at an aggregate flow rate of about 20 microliters per minute. FIG. 10D provides the same view as FIG. 10C, but shows the mixing pattern for mixing between two fluids at an aggregate flow rate of about 400 microliters per minute.

FIG. 11A is an exploded perspective view of a microfluidic mixing device constructed in five layers and capable of mixing two fluids, the device having ten through-layer contraction/expansion regions disposed in line with straight inlet and outlet channels. FIG. 11B is a top view of the assembled device of FIG. 11A. FIGS. 11C–11E are a top view photograph of the microfluidic mixing device of FIGS. 10A–10B with traced channel borderlines, showing the mixing pattern for mixing between two fluids at three different aggregate flow rates: 20, 200, and 400 microliters per minute, respectively.

FIG. 12A is an exploded perspective view of a microfluidic mixing device constructed in eleven layers and capable of mixing two fluids, the device having four stacked through-layer contraction/expansion regions with two flow reversals, the stacked regions disposed in line with straight inlet and outlet channels. FIG. 12B is a top view of the assembled device of FIG. 12A.

FIG. 13A is an exploded perspective view of a microfluidic mixing device constructed in five layers and capable of mixing two fluids, the device having eighteen through-layer contraction/expansion regions and sixteen 90-degree bends. FIG. 13B is a top view of the assembled device of FIG. 13A. FIGS. 13C–13E are a top view photograph of the microfluidic mixing device of FIGS. 13A–13B with traced channel borderlines, showing the mixing pattern for mixing between two fluids at three different aggregate flow rates: 20, 200, and 400 microliters per minute, respectively.

FIG. 14A is an exploded perspective view of a microfluidic mixing device constructed in five layers and capable of mixing two fluids, the device having two inlet channels that merge into a junction channel, an outlet channel disposed perpendicular to the junction channel, and a slit between the junction channel and outlet channel. FIG. 14B is a top view of the assembled device of FIG. 14A.

FIG. 15A is an exploded perspective view of a microfluidic mixing device constructed in five layers and capable of mixing two fluid streams, the device having inlet channels defined in two different device layers and defining multiple small holes that permit "streaks" of one fluid to be generated in the other fluid stream. FIG. 15B is a top view of the assembled device of FIG. 15A. FIGS. 15C is a top view photograph of the microfluidic mixing device having three holes according to the design of FIGS. 15A–15B, the photograph having traced channel borderlines and showing the mixing pattern for mixing two fluids at an aggregate flow rate of about 20 microliters per minute. FIG. 15D provides the same view as FIG. 15C of a very similar device having seven holes, also at an aggregate flow rate of about 20 microliters per minute.

FIG. 16A is an exploded perspective view of a microfluidic mixing device fabricated in three portions with conventional surface micromachining techniques and capable of mixing two fluids, the central portion defining multiple holes that permit "streaks" of one fluid to be generated in the other fluid stream. FIG. 16B is a top view of the assembled device of FIG. 16A.

DETAILED DESCRIPTION OF PREFERRED EMBODIMENTS OF THE INVENTION

Definitions

Figure 14C:
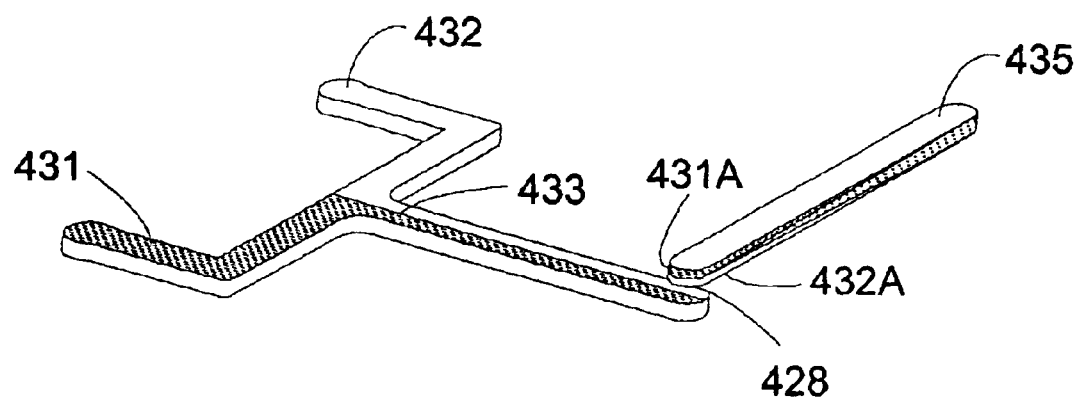
FIG. 14C is a schematic illustration of portions of the channels FIGS. 14A–14B showing the pattern of mixing between two fluids.

The term "channel" as used herein is to be interpreted in a broad sense. Thus, the term "channel" is not intended to be restricted to elongated configurations where the transverse or longitudinal dimension greatly exceeds the diameter or cross-sectional dimension. Rather, the term is meant to include a conduit of any desired shape or configuration through which liquids may be directed. A channel may be filled with one or more materials.

The term "major dimension" as used herein refers to the largest of the length, width, or height of a particular shape or structure. For example, the major dimension of a circle is its radius, and the major dimension of a rectangle (having a length that is greater than its width or height) is its length. As applied to an aperture, the major dimension of a circular aperture is its radius, and the major dimension of a typical rectangle is its length.

The term "microfluidic" as used herein is to be understood, without any restriction thereto, to refer to structures or devices through which fluid(s) are capable of being passed or directed, wherein one or more of the dimensions is less than 500 microns.

The term "overlap region" as used herein refers to a zone wherein fluid communication between two or more fluid streams is established, preferably wherein at least one channel extends over or past, or covers, a portion of another channel.

The terms "passive" or "passive mixing" as used herein refer to mixing between fluid streams in the absence of turbulent flow conditions and without the use of moving elements.

The term "stencil" as used herein refers to a material layer or sheet that is preferably substantially planar, through which one or more variously shaped and oriented channels have been cut or otherwise removed through the entire thickness of the layer, thus permitting substantial fluid movement within the layer (as opposed to simple through-holes for transmitting fluid through one layer to another layer). The outlines of the cut or otherwise removed portions form the lateral boundaries of microstructures that are completed when a stencil is sandwiched between other layers, such as substrates and/or other stencils. Stencil layers can be flexible, thus permitting one or more layers to be manipulated so as not to lie in a plane.

The term "substantially sealed" as used herein refers to a microstructure having a sufficiently low unintended leakage rate and/or volume under given flow, fluid identity, and pressure conditions. The term also encompasses microstructures that have one or more fluidic ports or apertures to provide fluid inlet or outlet utility.

Fabrication of Microfluidic Structures

In an especially preferred embodiment, microfluidic devices according to the present invention are constructed using stencil layers or sheets to define channels for transporting fluids. As described in further detail in co-pending U.S. application Ser. No. 09/453,029, a stencil layer is preferably substantially planar and has one or more microstructures such as channels cut through the entire thickness of the layer. For example, a computer-controlled plotter modified to manipulate a cutting blade may be used. Such a blade may be used either to cut sections to be detached and removed from the stencil layer, or to fashion slits that separate regions in the stencil layer without removing any material. Alternatively, a computer-controlled laser cutter may be used to cut patterns through the entire thickness of a material layer. While laser cutting may be used to yield precisely-dimensioned microstructures, the use of a laser to cut a stencil layer inherently removes some material. Further examples of methods that may be employed to form stencil layers include conventional stamping or die-cutting technologies. Any of the above-mentioned methods for cutting through a stencil layer or sheet permits robust devices to be fabricated quickly and inexpensively compared to conventional surface micromachining or material deposition techniques used by others to produce fluidic microstructures.

After a portion of a stencil layer is cut or removed, the outlines of the cut or otherwise removed portions form the lateral boundaries of microstructures that are completed upon sandwiching a stencil between substrates and/or other stencils. Upon stacking or sandwiching the device layers together, the upper and lower boundaries of a microfluidic channel within a stencil layer are formed from the bottom and top, respectively, of adjacent stencil or substrate layers. The thickness or height of microstructures such as channels can be varied by altering the thickness of a stencil layer, or by using multiple substantially identical stencil layers stacked on top of one another. When assembled in a microfluidic device, the top and bottom surfaces of stencil layers are intended to mate with one or more adjacent stencil or substrate layers to form a substantially sealed device, typically having one or more fluid inlet ports and one or more fluid outlet ports. A stencil layer and surrounding stencil or substrate layers may be bonded using any appropriate technique.

The wide variety of materials that may be used to fabricate microfluidic devices using sandwiched stencil layers include polymeric, metallic, and/or composite materials, to name a few. In especially preferred embodiments, however, polymeric materials are used due to their inertness and each of manufacture.

When assembled in a microfluidic device, the top and bottom surfaces of stencil layers may mate with one or more adjacent stencil or substrate layers to form a substantially sealed device. In one embodiment, one or more layers of a device may be fabricated from single- or double-sided adhesive tape, although other methods of adhering stencil layers may be used. A portion of the tape (of the desired shape and dimensions) can be cut and removed to form microstructures such as channels. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied. As an alternative to using tape, an adhesive layer may be applied directly to a non-adhesive stencil or surrounding layer. Examples of adhesives that might be used, either in standalone form or incorporated into self-adhesive tape, include rubber-based adhesives, acrylic-based adhesives, gum-based adhesives, and various other types.

Notably, stencil-based fabrication methods enable very rapid fabrication of robust microfluidic devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In another preferred embodiment, microfluidic devices according to the present invention are fabricated from materials such as glass, silicon, silicon nitride, quartz, or similar materials. Various conventional surface machining or surface micromachining techniques such as those known in the semiconductor industry may be used to fashion channels, vias, and/or chambers in these materials. For example, techniques including wet or dry etching and laser ablation may be used. Using such techniques, channels may be made into one or more surfaces of a first substrate. A second set of channels may be etched or created in a second substrate. The two substrates are then adhered or otherwise fastened together in such as way that the channels surfaces are facing one another and certain regions may be overlapped to promote mixing. One example of such a device is provided in FIGS. 7A–7B. A second example having an intermediate spacer layer is provided in FIGS. 16A–16B.

Still further embodiments may be fabricated from various materials using well-known techniques such as embossing, stamping, molding, and soft lithography. Additionally, in yet another embodiment, the layers are not discrete, but instead a layer describes a substantially planar section through such a device. Such a microfluidic device can be constructed using photopolymerization techniques such as those described in Cumpston, et al. (1999) Nature 398:51–54.

In addition to the use of adhesives or single- or double-sided tape discussed above, other techniques may be used to attach one or more of the various layers of microfluidic devices useful with the present invention, as would be recognized by one of ordinary skill in attaching materials. For example, attachment techniques including thermal, chemical, or light-activated bonding; mechanical attachment (including the use of clamps or screws to apply pressure to the layers); or other equivalent coupling methods may be used.

Microfluidic Mixers

The invention is directed to microfluidic mixing devices capable of rapidly mixing two or more fluid streams in a controlled manner without the use of stirrers or other moving parts. Typically, mixing is substantially completed within the novel microfluidic devices. In one embodiment, these devices contain microfluidic channels or channel segments that are formed in various layers of a three-dimensional structure. Mixing may be accomplished using various manipulations of fluid flow paths and/or contacts between fluid streams. For example, in various embodiments structures such as channel overlaps, slits, converging/diverging regions, turns, and/or apertures may be designed into a mixing device to promote rapid and controlled mixing between two or more fluid streams. Certain parameters may be altered to have a controllable effect on the amount or rate of mixing, such as, but not limited to, the amount of overlap, geometry of the overlaps, surface chemistry of the overlaps, the fluids used, and the flow rate of the fluids. Multiple structures to promote mixing may be used within the same device, such as to ensure more rapid or complete mixing, or to provide sophisticated mixing utility such as mixing different fluid streams in various proportions.

In one embodiment, a microfluidic device has at least two inlet channels on different substantially planar, horizontally disposed, layers of the device. Such layers can be flexible, such that the overall device does not lie in a plane. The layers containing the inlet channels can be adjacent or can be separated by one or more spacer layers. Where the layers are stencil layers, and the channels are cut through the entire thickness of the layers, the inlet channels should not overlap vertically until the overlap region, unless an intermediate spacer layer is used. The inlet channels meet at an overlap region. An outlet channel is provided that is in fluid communication with the overlap region, such that fluid flowing through the inlet channels must flow into the overlap region and exit through the outlet channel.

Microfluidic channels have at least one dimension less than about 500 microns. Channels useful with the present invention preferably also have an aspect ratio that maximizes surface-to-surface contact between fluid streams. A channel of the invention can have a depth from about 1 to about 500 microns, preferably from about 10 to about 100 microns, and a width of about 10 to about 10,000 microns such that the aspect ratio (width/depth) of the channel cross section is at least about 2, preferably at least about 10, at the overlap region where the channels meet. In various embodiments, a channel can be molded into a layer, etched into a layer, or can be cut through a layer. Where a channel is cut through the entire thickness of a layer, it is referred to as a stencil layer.

In one embodiment, two or more inlet channels are in fluid communication at an overlap region, with the overlap region also being in fluid communication with an outlet channel. The outlet channel can defined on or in the same layer as one of the inlet channels or can be defined on or in a different layer. In a preferred embodiment, the outlet channel is defined on or in a layer that is intermediately located between the inlet channels. In another embodiment, the outlet channel is a substantially continuous extension of one of the inlet channels.

Various embodiments produce sufficient interfacial contact per cross-sectional area between the different fluid streams to effect rapid mixing. In this manner, diffusional mixing is achieved between two or more fluid streams that meet at the overlap region, and they can mix to a greater degree than is usual in a microfluidic device. The shape and the amount of overlap at those points can be controlled in order to alter the amount of mixing.

In one embodiment, the device has two or more microfluidic inlet channels that are located on or in different layers of a three-dimensional device. The inlet channels are designed such that the flows of the fluids overlap, with a membrane or device layer separating the fluids from each other, and the flows are eventually channel in substantially the same direction. The inlet channels end at an overlap region where multiple fluid streams converge. The combined fluid flow then continues into the outlet channel that begins at the same overlap region. In one embodiment, the outlet channel is provided in a layer located between the two inlet channels, and is designed such that the direction of the resulting combined fluid flows in the same direction as the inlet fluids. An illustration showing fluid flow adjacent to the overlap region in such a device is provided in FIG. 9A. A first fluid stream flows (from right to left) through a first upstream channel 236, and a second fluid stream flows through a second upstream channel 237. Both the first and the second upstream (or inlet) channels 236, 237 slightly overlap a downstream (or outlet) channel 238. Both fluid streams pass from the respective upstream channels 236, 237 into the downstream channel 238. Initially, the first fluid fills the upper portion of the outlet channel 238 and the second fluid fills the lower portion of the outlet channel 238. However, since the width of the outlet channel 238 is much greater than its height, the two fluid streams share a large interfacial contact area across which diffusion occurs rapidly. Thus, complete mixing between the fluids occurs only a short distance downstream of the overlap region.

As an alternative to having inlet channels and an outlet channel all defined in different layers, the outlet channel may simply be a substantially continuous extension of one of the inlet channels. One example of such an embodiment is shown in FIG. 9B, which is discussed in further detail below.

In various embodiments, a microfluidic device may contain one or several of these fluidic overlaps. In certain embodiments, all of the fluidic mixers are substantially identical in type, size and/or geometry. In other embodiments, fluidic overlaps of different types, sizes, or geometries may be provided within a single device in order to produce preferential mixing. In certain embodiments, mixers may be multiplexed within a device to perform various functions. For example, mixers may be multiplexed within a device to promote combinatorial synthesis of various types of materials.

Importantly, the nature of these microfluidic mixers may be tuned for particular applications. Some of the parameters that affect the design of these systems include the type of fluid to be used, flow rate, and material composition of the devices. The microfluidic mixers described in the present invention can be constructed in a microfluidic device by controlling the geometry and chemistry of the regions where one fluid stream contacts another.

Prior two-dimensional microfluidic mixing devices typically have fluidic channels on a single substantially planar layer of a microfluidic device. Generally, the aspect (width to height) ratio of these channels is 10:1 or greater, with channels widths commonly being between 10 and 500 times greater than their height. This constraint is due in part to limitations of the silicon fabrication techniques typically used to produce such devices. In order to mix samples, two coplanar inlet channels are brought together into a common outlet channel. The fluids meet at the intersection and proceed down the outlet channel, typically in a side-by-side fashion. In microfluidic systems, fluid flow is practically always laminar (no turbulent flow occurs); thus, any mixing in this outlet channel occurs through diffusional mixing at the interface between the inputted liquid streams. This mixing is extremely slow since the interface between the two intersecting fluids is along the smaller dimension of the perpendicular cross-sections of the fluid streams, and this dimension is very small compared to the overall volume of the fluids. Since in traditional two-dimensional microfluidic systems all of the fluidic channels are contained within the same substantially planar layer of the device, this problem is difficult to overcome. A microfluidic device approximating prior art two-dimensional mixing structures was constructed and is shown in FIGS. 3A–3B and 4A–4B. As shown in fairly dramatic fashion in FIGS. 4A–4B, using conventional methods to attempt to mix two different microfluidic streams generally does not yield rapid and complete mixing.

Microfluidic devices according to the present invention are three-dimensional, having microfluidic channels defined on or located in different layers of a fluidic device. In certain embodiments, inlet channels carrying streams of different fluids are provided in different layers, and these layers are stacked vertically. When microfluidic channels defined on or in different layers merge in an overlap region to supply multiple fluid streams into a common (outlet) channel, a combined stream having at least one interface between the two fluids is created. In certain preferred embodiments, this interface is along the largest cross-sectional dimension of the outlet channel perpendicular to the direction of fluid flow, such as along the entire width of the outlet channel. This large interface maximizes the diffusion area between the different fluids. In this manner, the majority of the volume of each fluid is in very close proximity to the fluid-fluid diffusion interface and mixing occurs very rapidly. Importantly, the nature of these overlap regions should be carefully controlled in order to optimize the mixing, as will be described below.

In the embodiment shown in FIGS. 1A–1B, a microfluidic mixing device 10 is constructed with a sandwiched stencil construction method. A first layer 11 defines two inlet ports 16, 17 and an outlet port 18. The second (stencil) layer 12 defines two vias 21, 22 (in fluid communication with one inlet port 17 and the outlet port 18, respectively) and a channel 20 for delivering one fluid to an overlap region 26. The third (stencil) layer 13 defines a channel 24 and a via 23 aligned with the via 21 in the second layer. The fourth (stencil) layer 14 defines a single channel 25. The fifth layer 15 is a substrate that serves as the lower boundary of the channel 14 defined in the fourth layer 14. Each of the channels 20, 24, 25 have a nominal width of about eighty (80) mils, and each of the ports 16–18 and vias 21–24 have a nominal diameter of about 140 mils. Notably, the three channels 20, 24, 25 meet at an overlap region 26, as shown in FIG. 1B. That is, the first inlet channel 20 in the second stencil layer 12 overlaps the outlet channel 24 in the third stencil layer 24 from above, and the second inlet channel 25 in the fourth stencil layer 14 overlaps the outlet channel 24 in the third stencil layer 24 from below. Both the first inlet channel 20 and the second inlet channel 25 are substantially upstream of the overlap region 26, and the outlet channel 24 is substantially downstream of the overlap region 26. Immediately upstream of the overlap region 26, each of the fluid streams contained in the channels 20, 25 is directed in substantially the same direction, and the combined streams proceed in the same direction just downstream of the overlap region 26 in the outlet channel 24.

In use, a first fluid stream is injected into the first inlet port 16 and into the first inlet channel 20. A second fluid stream is injected into the second inlet port 17, then flows through vias 21, 23 into the second inlet channel 25. The two fluid streams meet at the overlap region 26, at which point they are forced to converge into a single outlet channel 24. As the fluids meet and pass into the outlet channel 24, just downstream of the overlap region 26 the upper half of the channel 24 contains the first fluid and the lower half of the channel 24 contains the second fluid. Since the height of each the channels 20, 24, 25 is relatively small (between 100 nm and 500 microns), diffusional mixing occurs quickly in the outlet channel 24 and a homogenous material is transported off of the device 10 at exit port 18. It has been discovered that the majority of the mixing occurs right at the overlap region 26, with a slight amount of mixing occurring within channel 24 immediately after the overlap region 26. The amount of mixing that occurs after the junction point 33 depends on a number of factors, including geometry of the channels, chemical make-up of the channels and fluid samples, and fluid flow rates.

In the embodiment shown in FIGS. 1A–1B, the three channels that converge at the overlap region 26 are all the same width. Surprisingly, it has been discovered that if the stencil layers defining the channels are not well aligned in the resulting device, then proper mixing between the fluid streams does not occur. The resulting fluid in the outlet channel 26 is a mixture of the two input fluids only at points where channels 20, 24, and 25 all overlap. If, for example, the second inlet channel 25 is misaligned laterally such that for a small portion of the overlap region 26 there is an area where only the first inlet channel 20 and the outlet channel 24 overlap, then in this region only the fluid from the first inlet channel 20 will enter the outlet channel 24. The remainder of the fluid entering outlet channel 26 will be a mixture of the two input fluids; this will cause a detrimental "streaking" effect, where a flow of mixed fluids runs parallel with an unmixed fluid through the outlet channel 24. Such "streaking" problems are easily overcome by the following modifications.

Preferred mixer embodiments are shown in FIGS. 2A–2B. These embodiments do not suffer from the same strict alignment parameters as the mixer shown in FIGS. 1A–1B. Referring to FIG. 2A, three different microfluidic mixers 51–53 are built into a single device 30. The device is constructed from five layers 31–35, including three stencil layers 32–34. The first uppermost layer 31 defines inlet ports 36, 37 and outlet ports 38 for each of the three mixers 51–53. The second stencil layer 32 defines vias 39, 40 for each mixer along with three inlet channels 41, 42, 43, one for each mixer 51–53. The third stencil layer 33 defines vias 44 for each mixer and three outlet channels 45. The fourth layer 34 defines a further inlet channel 48, 49, 50 for each mixer 51–53. The fifth substrate layer 35 encloses the inlet channels 48–50 from below and may serve as a rigid support for the device 30. The various ports 36–38 and vias 39, 40, 44 each have a nominal diameter of about one hundred forty (140) mils. Each of a the various channels have a nominal width of about eighty (80) mils.

As shown in FIG. 2B, the various layers 31–35 are adhered together to form the completed device 30. Notice that the shapes of the overlap regions 55–57 in these mixers 51–53 are shaped so that slight misalignment of layers during construction will not greatly affect fluid flow and mixing. Namely, he leftmost outlet channel 45 has a narrowed portion 45A, while upstream channels 42, 43, 49, 50 have wider portions 42A, 43A, 49A, 50A, respectively, in a couple of configurations to provide the same effect. The narrowed portion 45A is about 40 mils wide; the wide portions 43A, 50A are about one hundred eighty (180) mils wide; and the wide portions 42A, 49A have a nominal diameter of about 140 mils. The result of these modifications is that at each overlap regions 55–57, the upstream channels are slightly wider than the downstream channels. It has been found that mixers such as shown in FIGS. 2A–2B are far superior to the mixer shown in FIGS. 1A–1B, for the reason noted above.

In another preferred embodiment, changing the chemical nature in the overlap region alters the overlap junction. This can be accomplished by forming a stencil layer from a different material, or by altering the surface chemistry of a stencil layer. Surface chemistry of a stencil layer can be altered in many ways, as would be recognized by one skilled in the art. Examples of methods for altering surface chemistry include chemical derivatization as well as surface modification techniques such as plasma cleaning or chemical etching. The chemical derivatization is preferably chosen such that fluid flow through the channels and overlap region occurs smoothly and without bubble formation.

The above-described methods for altering the overlap region within a microfluidic device can be used independently or in conjunction with one another. Other methods for altering the nature of the overlap are also contemplated within the present invention, if not specifically stated herein.

One surprising aspect of the present invention is that the optimal parameters for a given overlap are greatly affected by the nature of the fluid sample that is to be used within the device. It has been found that the optimal geometry for these overlaps changes depending upon the solution used.

The mixing between two or more fluid channels can be adjusted to give a tremendous range of different ratios. The main or easiest way to do this is to hold the flow rate of one channel constant, while adjusting the flow rate of the other channel. In this way, different mixture ratios are formed by virtue of different quantities of each liquid entering the mixing chamber/overlap area in a given time period. Another method of adjusting the mixing ratio is to alter the size of the channels leading into the mixing region; this has the effect of changing the flow rate internally. This would be useful for applications such as arrays, where different ratios are desired without the hassle of supplying fluids at many different external flow rates.

In a preferred embodiment, more than two fluids may be mixed at an overlap region. One example showing the mixing of three fluids at a single overlap region is provided in FIGS. 5A–5B. In another preferred embodiment, multiple overlap regions may be provided in series such that a first overlap region produces a first mixture, and subsequent overlap regions produce further mixtures. One example of multiple overlap regions used within a single device is shown in FIGS. 6A–6B, which provides a mixing device capable of mixing two fluid streams in various proportions.

In a preferred embodiment, a microfluidic mixer includes a spacer layer having at least one aperture along an overlap region for communicating fluid from one microfluidic channel to another. Apertures in spacer layers may be provided in various shapes and configurations. In one such embodiment, an aperture may be configured in the shape of a slit. If the inlet and outlet channels direct fluids in substantially the same direction, then a slit in an intermediate spacer layer is preferably oriented substantially perpendicular to the direction of fluid flow. Additionally, a slit configured in this manner is preferably at least at long in major dimension as the greater of the width of the inlet or outlet channels in fluid communication with the slit. Such a configuration is useful to promote contact between at least two fluid streams along the entire width of an overlap region. One example of a mixing device having a slit defined in an intermediate spacer layer is provided in FIGS. 8A–8B. A further illustration showing fluid flow adjacent to the overlap region in such a device is provided in FIG. 9B. A first fluid stream flows (from right to left) through a first upstream channel 231, and a second fluid stream flows through a second upstream channel 232. The first fluid passes through a slit 233 that overlaps the inlet/outlet channel 232, 234 and joins the second fluid in an outlet channel 234. In this particular embodiment, the outlet channel 234 is a continuous extension of the second inlet channel 232.

In another mixer embodiment having an intermediate spacer layer, the spacer layer defines an aperture that is substantially smaller in major dimension than the adjacent channels. Such an aperture may be configured in various convenient shapes, such as round, rectangular, or triangular, to name a few. Additionally, such an aperture is preferably disposed substantially centered along the width of each of the adjacent channels. In one embodiment, two microfluidic channels carrying different fluids meet at a junction region in one layer, which typically results in a combined stream of two distinct fluids flowing side-by-side. The combined stream then proceeds through an "upstream" channel to a channel overlap region with a small aperture that permits fluid communication between the upstream channel and a downstream channel. Flow continues through the small aperture and into the downstream channel. The combination of the small aperture and downstream channel serves as a contraction/expansion region, since fluid flow area contracts through the aperture and then expands as fluid moves into the downstream channel. Multiple channel overlap contraction/expansion regions may be provided in a single device. When placed in series, multiple contraction/expansion regions may promote more rapid or complete mixing of multiple fluids. Some examples of mixing devices having multiple channel overlap contraction/expansion regions are provided in FIGS. 10A–10B and 11A–11B. In further embodiments, fluid streams may be manipulated to undergo a substantial change in direction from one contraction/expansion region to another. Examples of such devices are provided in FIGS. 12A–12B and 13A–13B.

Yet another embodiment having an intermediate spacer layer includes an aperture configured in the shape of a slit that is disposed substantially parallel to the direction of fluid flow upstream of an overlap region, and substantially perpendicular to the direction of fluid flow downstream of the overlap region. A first fluid and a second fluid meet at a junction region and flow side-by-side into a common channel upstream of the slit. The channel immediately downstream of the slit is substantially perpendicular to the upstream channel, with the major dimension (e.g., length) of the slit preferably being at least as long as the width of the downstream channel. The combined stream of the two side-by-side fluids flow through the slit and is "folded" into the downstream channel such that one fluid is layered substantially on top of the other fluid. Since the width of the downstream or outlet channel is much greater than its height, layering the two fluid streams vertically provides a large interfacial contact area that facilitates rapid diffusional mixing just downstream of the slit. An example of such a "folding" mixing device is illustrated in FIGS. 14A–14B, with a schematic of fluidic interaction inside such a device provided in FIG. 14C.

In another embodiment, an intermediate spacer layer includes multiple apertures for communicating fluid from a first (upstream) channel to a second (downstream) channel. Preferably, each aperture has a major dimension (e.g., diameter) that is substantially smaller than the width of the first channel or the second channel. For example, each aperture is preferably less than about one-quarter the width of the first channel or the second channel, more preferably less than about one-eighth, and more preferably still less than about one-sixteenth. In absolute terms, each aperture preferably has a major dimension (e.g., diameter) of less than about 200 microns; more preferably less than about 100 microns, and more preferably still less than about 50 microns. The multiple apertures are preferably distributed along the width of the upstream and downstream channels, such that a first fluid that is supplied by the upstream channel through the apertures generates beneficial "streaks" within (rather than alongside) a second fluid supplied to the downstream channel. This beneficial streaking of the first fluid within the second fluid generates a large interfacial contact area between the two fluids that promotes rapid diffusional mixing. One example of a mixing device having multiple small apertures is shown in FIGS. 15A–15B, the device being constructed using a sandwiched stencil construction method. A microfluidic mixing device that functions according to the same principles may also be constructed from rigid materials such as silicon or glass using surface micromachining techniques, as illustrated in FIGS. 16A–16B.

The following Examples describe certain aspects of several preferred embodiments of the present invention and are not intended to be limiting in any manner. Rather, the scope of the present invention is defined by the claims appended hereto.

EXAMPLE 1

In this example, the mixing characteristics of various microfluidic mixers according to conventional designs are compared against one microfluidic mixer according to the present invention. Referring to FIGS. 3A–3B, a single device 60 containing four independent microfluidic mixers 90–93 was constructed. The device 60 was constructed from five layers 61–65 (including sandwiched stencil layers 62–64) to demonstrate the novel overlap mixer 90, but the mixers 91–93 approximated conventional 2-dimensional surface micromachined mixers. Applicants are not aware of the construction of conventional mixers such as those illustrated (e.g., mixers 91–93) by others using a sandwiched stencil construction method. The first layer 61 served as a cover layer, defining fluidic inlet ports 66, 67 and outlet ports 70, 71 for each of the three conventional-type mixers 91–93, further defining inlet ports 68, 69 and outlet ports for the novel overlap mixer 90. The second layer 62 defined channels 74, 75, 76 for the conventional-type mixers 91–93 along with a first inlet channel 77 and three vias 78, 79, 80 for the novel overlap mixer 90. The third layer 63, which served as a lower boundary for the channels 74–77 defined in the second layer 62, further defined a via 82 and an outlet channel 81 for the novel overlap mixer 90. The fourth layer 64 defined a second inlet channel 83 for the overlap mixer 90, while the fifth layer 65 was a bare substrate enclosing the second inlet channel 83 from below and generally supporting the device 60. The uppermost layer 61 and the stencil layers 62–64 were constructed from layers of single sided tape (3 mil polypropylene carrier with water based adhesive on one side) and each of the channels 74–77, 81, 83 had a nominal width of about sixty (60) mils. The bottom layer 65 was a 0.25 inch thick acrylic substrate. Inlet ports 92,93 and outlet ports 94,95 are placed in the upper most stencil layer. All inlet/outlet ports and vias were approximately sixty (60) mils in diameter, with the various channels each having a nominal width of about forty-five (45) mils. The layers 61–65 were adhered together to form the completed device 60, shown in FIG. 3B.

Operation of the different mixers within the device 60 will now be described, starting with the conventional-type mixers 91–93. Due to the channel dimensions, all of the fluid flow through the channels of the device 60 is laminar in nature. If two different fluids are injected into the two inlet ports 66, 67 of the topmost mixer 93 (topmost in FIG. 3B), the fluids travel through the converging independent channel segments and meet at the central section of channel 74. Since the fluid flow is laminar and the interfacial contact area between the two fluid streams is relatively small (owing to the small channel height relative to its width), very little mixing occurs as the fluids travel down their respective sides of the central channel until it splits into two channel segments leading to the outlet ports 70, 71. Surprisingly, the fluid that entered the device 60 through the inlet port 66 exits almost completely out of the outlet port 70, and the fluid that entered the inlet port 67 exits almost completely out of the outlet port 71. The only mixing that occurred in the central area of the channel 74 was through diffusional mixing at the relatively small interface of the liquids. Since these channels are very wide (about 60 mils) but not very high (about 4 mils), the interfacial contact area between the two fluids is very small and the molecules at the interface of the two fluids would have to diffuse up to 30 mils in order for complete mixing to occur. At room temperature, diffusional motion is not sufficiently rapid for substantial mixing to occur along this interface.

The mixer 93 can be improved slightly by lengthening the channel 75, thereby extending the interfacial contact area between the two fluids, as in mixers 75 and 76. In both of these slightly improved mixers 75, 76, the length of the mixing region is extended. However, very little mixing occurs even in these "improved" mixers. Another method to possibly increase mixing is to supply the fluid streams to the device at slower flow rates, to allow more time for the diffusion process to occur. However, this still results in incomplete mixing over any reasonable time period.

As an alternative to the conventional-type mixers 91–93, a microfluidic overlap mixer 90 according to the present invention is also provided in the device 60. In this mixer 90, inlet channels 77, 83 were constructed on different layers of a three-dimensional structure. The inlet channels 77, 83 are in fluid communication at the overlap region 95 where the two fluids to be mixed are forced to enter into outlet channel 81, in this case defined in a layer 63 intermediate to the layers 62, 64 containing the two inlet channels 77, 83. In this embodiment, the interfacial contact area between the two fluids at the overlap region extends all the way across the width of the outlet channel 81 (upstream of the channel fork) and this contact area is fifteen (15) times greater per unit length than in the previously-described mixer 93. Additionally, the greatest distance that the molecules need to diffuse in order for mixing to occur is now only about two (2) mils, rather than thirty (30) mils as in the previous mixer 93.

Mixing behavior in the novel overlap mixer 90 was demonstrated by performing a simple acid-base reaction. A 0.1 molar NaOH solution was injected through the first inlet port 68 and into the first inlet channel 77, and a 0.5M HCl solution injected through the other inlet port 69 into the other inlet channel 83. The NaOH solution contained a small amount of bromophenol blue indicator (which is purple in basic solution, and yellow in acidic solution). Upon entering the overlap region 95, the clear HCl solution and dark-purple NaOH solution mixed and reacted completely as evidenced by the color change of the indicator to a deep golden color (i.e., the stronger acidic solution neutralized the weaker basic solution, and the resulting mixture was weakly acidic).

Mixing was also demonstrated using a 0.1 molar HCl solution mixing with a 0.2 molar (clear) NaOH solution, in which the indicator was first dissolved in the acidic HCl solution. A mixture between the clear NaOH solution and yellow HCl solution would yield a dark purple fluid (in this case, the weaker acid is neutralized by the stronger base, resulting in a mixture that is weakly basic). First the overlap mixer 90 according to the present invention was tested. The clear NaOH solution was supplied to the first inlet port 68 and a yellow HCl solution (containing indicator) was supplied to the second inlet port 69. The two fluids flowed through the inlet channels 77, 83 and began to mix at the overlap region 95. The mixing was nearly complete immediately downstream of this region 95. Dark fluid color was observed within the downstream channel 81 and at the outlet ports 72, 73, which was indicative of the acid-base reaction going to completion. In comparison, the conventional-type mixers 91–93 were also tested using these same solutions. In these tests, little or no mixing occurred along the entire interface of the two fluids. The solutions that emerged from the separate outlets of each mixer were the same color and pH as the separate solutions that were supplied at the corresponding inlet side.

The mixing behavior was also demonstrated by injecting water that had been dyed yellow into inlet port 66 and a blue-dyed fluid into the other inlet port 67 of each conventional mixing device 91–93, and injecting the same fluids into the inlet ports 68, 69 of the novel overlap mixer 90. In the conventional mixers 91–93, the two fluids flowed side-by-side through the channels 74, 75, 76 and no mixing occurred. For example, referring to FIG. 4A, yellow fluid was injected into inlet port 67 and blue fluid was injected into inlet port 66 of the first conventional-type mixer 93, and mixing between the two fluids was not observable through-out the length of the channel 74. Another example of unsuccessful mixing in a conventional-type mixer 92 is illustrated in FIG. 4B. The same two fluids were injected through ports 66, 67 into a snaking channel 75; still no or only very slight mixing occurred. Finally, referring to FIG. 4C, the colored fluids were provided to the novel overlap mixer 90. The two fluids proceeded through the inlet channels 77, 83 to the overlap region 95. The two fluids begin to mix at the overlap region 95 and mixing was complete just after this region 103, as apparent by the green color of the resulting fluid.

EXAMPLE 2

In one embodiment of the present invention, more than two fluids may be mixed in a single overlap region. For example, FIGS. 5A–5B illustrate a microfluidic mixing device 100 that receives and mixes three different fluid streams. The mixing device 100 is constructed in seven layers 101–107, including stencil layers 102, 104, 106. The first layer 101 defines three fluid inlet ports 108–110 and a single fluid outlet port 112. The second layer 102 defines a first fluid inlet channel 114 and vias 115, 116, 118. The third layer 103 defines three vias 119–121 and a first wide (large) slit 122. The fourth layer 104 defines one via 125 and an inlet/outlet channel 124. The fifth layer 105 defines a via 126 and a second wide slit 127. The sixth layer 106 defines a third fluid inlet channel 128. The seventh layer 107 is a bare substrate that serves as the lower boundary of the channel 128 and serves to support the device 100. All of the channels have a nominal width of about sixty (60) mils, and each of the various vias and ports are about eighty (80) mils in diameter. The slits 122, 127 are about one hundred twenty (120) mils in length, and about fifty (50) mils wide. The upper layers 101–106 are all constructed from single sided tape (3 mil thick polypropylene backing with water based adhesive). The bottom layer 107 is a 0.25 inch thick block of acrylic. The assembled device 100 is shown in FIG. 5B.

In use, streams of three different fluid streams injected into the device 100 through the inlet ports 108–110. Each of the fluid streams travels down their respective inlet channels 114, 124, 128 and meet at the overlap region 130. The upper channel 114 supplies fluid to the outlet channel 124 through the first wide slit 122, and the lower channel 128 supplies fluid the outlet channel 127 through the second wide slit 127. Notably, the length of each of the wide slits 122, 127 is greater than the width of the central inlet/outlet channel 124. In the overlap region 130, the fluid from the upper channel 114 is forced into the top third of the outlet portion of channel 124 (downstream of the overlap region 130); the fluid from the inlet portion of the channel 124 occupies the middle third of the outlet portion of channel 124; and fluid from the lower channel 128 occupies the bottom third of the outlet port of the channel 124. As before, a large interfacial contact area is established between each fluid in the overlap region 130 and the channel 124 downstream of the region 130 to promote very rapid diffusional mixing between the various streams, so that the fluid that exits the device 100 through the outlet port 112 is fully mixed. This device 100 also allows for a tremendous range in the mixing ratios. The flow rates of each of the fluids can be adjusted to allow a greater or lesser amount of each fluid to be added to the resulting mixture.

EXAMPLE 3

In one embodiment, multiple fluid input streams may be simultaneously mixed in different proportions to yield a greater number of output streams. For example, a microfluidic multi-mixing device 140 is shown in FIGS. 6A–6B. This mixing device 140 receives two different fluids as inputs and is capable of providing four different fluid streams as outputs. The device 140 is constructed from five layers 141–145, including stencil layers 142–144. The first layer 141 defines two inlet ports 152, 153 and four outlet ports 154–157. The second layer 142 defines vias 158,159 and five channel segments 160 having rounded portions. The third layer 143 defines two forked inlet channels 162, three intermediate splitting channels 163, and four outlet channels 164. The fourth layer 144 defines five more channel segments 165 having rounded portions. The fifth layer 145 is a bare substrate that encloses the channel segments 165 from below and provides support for the device 140. The forked inlet channels 162 and intermediate splitting channels 163 are about forty-five (45) mils wide, while the channels 164 and segments 160, 165 have a nominal width of about fifteen (15) mils. All of the ports 152–157, vias 158, 159 and rounded portions have nominal diameters of about seventy (70) mils. The upper four layers 141–144 are all constructed from single sided tape (3 mil thick polypropylene backing with water based adhesive). The lower layer 145 is a bare substrate such as 0.25 inch thick acrylic.

In use, fluid A is injected at port 152 and fluid B at port 153. Each of the fluid streams is split in the forked regions of the channels 162. Just upstream of the intermediate splitting channels 163, there exist three fluid (sub)streams. The leftmost stream is a substream of fluid B; the rightmost stream is a substream of fluid A; and at the overlap region 168, substreams of fluids A and B mix to form an A+B mixture. The three fluid streams proceed to the intermediate splitting channels 163, through the segments 160, 165 and to the next set of overlap regions 169, 170. At one overlap region 169, the two inputs are pure A and a mixture of A+B. The resulting output into the outlet channel 156 is 3A+B. At the other overlap region 170, A+B mixes with pure B, resulting in a mixture of 3B+A at the outlet channel 155. Pure fluid A flows through the rightmost outlet channel 157, while pure fluid B flows through the leftmost outlet channel 154. Other combinations can be constructed. In practice, the amount of fluid mixing at each of the output channels is dependent on a number of factors, including flow rate, fluid properties and device geometry and chemistry.

EXAMPLE 4

In one embodiment, a spacerless microfluidic overlap mixing device may be constructed using surface miromachining techniques such as those developed for fabricating silicon devices. Referring to FIGS. 7A–7B, a mixing device 175 is fabricated from two substrates 180, 182. A channel 181 is patterned in the upper surface 187 of a first <110> Si substrate 180 using an oxide mask and etched in 70° C. KOH. The channel 181 is etched so that it is about 100 microns wide and about 3 microns deep. A second channel 183 is similarly patterned and etched in the lower surface 188 of another <110> Si substrate 182. Holes 184–186 are drilled all the way through the second substrate 182 to access the channels 181, 183. These holes are approximately 800 microns in diameter. The two substrates 180 and 182 are aligned face-to-face and the two surface 187, 188 are anodically bonded together to form a substantially sealed microfluidic mixing device as shown in top view in FIG. 7B.

In use, a first fluid is injected into the first inlet port 184 and a second fluid is injected into the second inlet port 185. The fluids each travel down their respective channels 181, 183 and meet at the overlap region 189. Again, the interfacial contact area between the two fluids is maximized in the overlap region 189 and diffusional mixing occurs very rapidly, so that the combined stream is fully mixed by the time it reaches region 190 downstream of the overlap region 189.

EXAMPLE 5

In one embodiment, a microfluidic overlap mixer includes a spacer layer defining a slit permitting fluid flow therethrough. Referring to FIGS. 8A–8B, a microfluidic mixing device 200 may be fabricated in five layers 201–205, including stencil layers 202, 204. The first layer 201 defines two inlet ports 206, 207 and an outlet port 208, each about 100 mils in diameter. The second layer 202 defines two vias 209, 210 and a channel 211. The channel 211 includes two turns leading to a channel portion 212 that directs the fluid in substantially the same direction as the outlet channel 225. The downstream end 213 of the portion 212 is enlarged in the shape of a rectangle positioned above the slit 220 in the third (spacer) layer 203. This enlarged downstream end 213 overlaps the inlet/outlet channel 222, 225. The narrow slit 220 may be constructed without removing material by cutting a third layer 203 with a blade. Alternatively, the slit 220 may be formed by laser cutting, die cutting, or other equivalent means. Preferably, the slit 220 is longer than the width of the inlet channel 222 and the outlet channel 225 adjacent to the slit 220. The third layer 203 further defines two vias 216, 218. The fourth layer 204 defines an inlet channel 222 substantially upstream of the slit 220 and an outlet channel 225 substantially downstream of the slit 220, with the outlet channel 225 being a continuous extension of the inlet channel 222. The aforementioned channels each The fifth layer 205 is a bare substrate that encloses the inlet/outlet channel 222, 225 from below and serves to generally support the other layers 201–204 of the mixing device 200.

Preferably, the second and fourth stencil layers 202, 204 are fabricated from a material having adhesive on both sides, such as, for example, a one (1) mil thick polypropylene film having a 2.4 mil thick integral layer rubber-based pressure-sensitive adhesive on both sides (Avery Dennison, Brea, Calif.). This permits the first, third, and fifth layers 201, 203, 205 to be fabricated from non-adhesive layers. For example, the first and third layers 201, 203 may be fabricated from one (1) mil thick adhesiveless polypropylene film, and the fifth layer 205 may be constructed from a similar film or a more rigid (generally thicker) substrate. The result of constructing the layers 201, 203, 205 that sandwich the stencil layers 202, 204 from adhesiveless materials is that the upper and lower boundaries of the channels 211, 212, 222, 225 lack any adhesive coating. Since the width of each of these microfluidic channels is much greater than their height, this greatly reduces any potential interaction between adhesive and the fluidic contents of the mixing device 100, since the only adhesive surfaces that may contact the fluid(s) are along the lateral walls of the channels. Another advantage of constructing the mixing device 200 with non-adhesive sandwich layers 201, 203, 205 is that it avoids the possibility of inadvertent permanent collapse of the channels 211, 212, 222, 225 in case compressive pressure is applied to the device or the channels experience sub-atmospheric fluid pressure that might draw any of the sandwich layers 201, 203, 205 into contact with one another within the channels.

In operation, a first fluid stream is injected into the first inlet port 206, and a second fluid stream is injected into the second inlet port 207. The first fluid stream enters the first upstream channel 211, turns twice to be directed by channel portion 212 to flow in substantially the same direction as the outlet channel 225 before entering the enlarged rectangular end portion 213. At the same time, the second fluid stream flows through the vias 209, 216 and into the second upstream channel 222. The first fluid stream is forced from the end region 213 through the slit 220 to join the second stream in the outlet channel 225. In the outlet channel 225, the first fluid is layered atop the second fluid across the entire channel width and mixing occurs very rapidly. The resulting mixture flows to the end of the outlet channel 225 then through the vias 218, 210 and the outlet port 208 to exit the device 200.

EXAMPLE 6

In one embodiment, a microfluidic mixing device includes a spacer layer defining an aperture that is substantially smaller in diameter than the adjacent upstream and downstream channels, such that the aperture and downstream channel serve as a contraction/expansion region to promote mixing. One example of a microfluidic mixer embodying such a design is shown in FIGS. 10A–10B. A mixing device 250 is constructed in five layers 251–255, including stencil layers 252, 254. Starting from the bottom, the first layer 251 defines two fluid inlet ports 256, 257 and two outlet ports 258, 259, each port being about eighty (80) mils in diameter. The second layer 252 defines two inlet channel sections 260, 261 meeting at a junction 262 that feeds an upstream channel section 263. The second layer 252 defines another channel 264 having a splitting region 265 for dividing a mixed fluid stream into two substreams. The third layer 253 defines two small apertures 266, 267, each aperture being smaller in size than the adjacent channels 263, 268, 264. In this embodiment, each of the apertures 266, 267 are approximately six (6) mils in diameter. Preferably, these apertures 266, 267 are substantially centered along the width of each of the channels 263, 264, 268. The fourth layer 254 defines a channel 268 that slightly overlaps both channel section 263 and channel 264 defined in the second layer 252. The channel 268 is substantially downstream of the channel section 263 and first aperture 266, and simultaneously is substantially upstream of the second aperture 267 and channel 264. The fifth layer 255 may be fabricated from a bare substrate or film, thus serving to enclose the channel 268 from above and support the device 250 if necessary. The channels 260, 261, 263, 264, 265, 268 each have a nominal width of about forty (40) mils. As described in connection with the previous Example, the stencil layers 252, 254 may be advantageously fabricated from double-sided self-adhesive tapes, while the sandwiching layers 251, 253, 255 may be fabricated from non-adhesive materials.

In operation, a first fluid stream is injected into the first inlet port 256 and a second fluid stream is injected into the second inlet port 257. The fluid streams travel through channel sections 260, 261, respectively until they meet at a junction 263. From the junction, the components of the combined stream flow side-by-side through the channel section 263 until reaching the first aperture 266. The combined stream flows upward through the small aperture 266 and into channel 268, which together serve as a contraction-expansion region that promotes mixing. The combined stream proceeds through channel 268 and flows downward to the second aperture 267 and into the channel 264. The combination of the second aperture 267 and the channel 264 serves as another contraction-expansion region that promotes further mixing. In the illustrated embodiment, the first upstream channel section 263, the upstream/downstream channel section 268, and the downstream channel section 264 all direct the fluids in substantially the same direction without any significant directional change. From the second channel 264, the fluid is directed to a splitting region 265 where it is split into two streams to exit the mixing device 250 through outlet ports 258, 259.

It has been observed that the microfluidic mixing device 250 promotes more rapid or complete mixing within a given distance of the contraction/expansion regions at higher fluid flow rates. For example, FIG. 10C shows a photograph of a combined fluid flow rate of about twenty (20) microliters per minute flowing through the device 250 (flowing from left to right). Notably, mixing does not appear complete downstream of the contraction/expansion regions, since a relatively clear demarcation between the first (blue) and second (yellow) fluid streams remains visible. In contrast, FIG. 10D shows a photograph of the same device subjected to a combined fluid flow rate of about four hundred (400) microliters per minute. In this case, mixing between the fluid streams appears to be much more complete.

EXAMPLE 7

In the previous example, a microfluidic mixing device included two contraction/expansion region. Similar mixing devices can be constructed with numerous contraction/expansion devices in series to promote more rapid or complete mixing. For example, a microfluidic mixing device 300 having ten (10) contraction/expansion regions is illustrated in FIGS. 11A–11B. The device 300 is constructed in five layers 301-305, including stencil layers 302, 304. Starting from the bottom, the first layer 301 defines two fluid inlet ports 308, 309 and two outlet ports 310, 311, each port being about eighty (80) mils in diameter. The second layer 302 defines two inlet channel sections 312, 313 meeting at a junction 314 that feeds an upstream channel section 315. The second layer 302 defines four channel sections 315 and another channel 316 having a splitting region for dividing a mixed fluid stream into two substreams. The third layer 303 defines ten (10) small apertures 318, each aperture 318 being about six (6) mils in diameter. As before, these apertures 318 are substantially centered along the width of each of the channels 315, 316, 320. The fourth layer 304 defines five channel sections 320, each of which slightly overlaps two channels or channel sections defined in the second layer 302. Each of the channel sections 315, 320 is downstream of one aperture 318 and upstream of another, with the channel sections 315, 320 and upstream and downstream channels 314, 316 all serving to direct fluid in substantially the same direction. The fifth layer 305 may be fabricated from a bare substrate or film, thus serving to enclose the channel sections 320 from above and support the device 300 if necessary. Each of the above-described channels has a nominal width of about forty (40) mils. As described in connection with the previous two Examples, the stencil layers 302, 304 may be advantageously fabricated from double-sided self-adhesive tapes, while the sandwiching layers 301, 303, 305 may be advantageously fabricated from non-adhesive materials.

The mixing device 300 operates in a substantially identical manner as the device 250 described previously, except that the device 300 has ten (10) contraction/expansion regions rather than two. It has been observed that the use of ten additional contraction/expansion regions promote more rapid or complete mixing than the use of two. As before, better mixing was observed at higher fluid flowrates, as shown in FIGS. 11C–11E. FIG. 11C shows a photograph of a combined fluid flow rate of about twenty (20) microliters per minute flowing through the mixing device 300 (flowing from left to right). Here, a relatively clear demarcation between the first (blue) and second (yellow) fluid streams remains visible even after passage through ten contraction/expansion regions, indicating less-than-optimal mixing. FIG. 11D shows a photograph of the same device 300 containing a combined fluid flow rate of about two hundred (200) microliters per minute. Mixing appears to be noticeably better in this case. FIG. 11E, however, shows the same mixing device 300 with better mixing results obtained at a combined fluid flow rate of about four hundred (400) microliters per minute. It thus appears that higher fluid flow rate and the presence of more contraction/expansion regions are factors that may be employed to improve mixing.

EXAMPLE 8

In further embodiments, fluids may undergo substantial directional changes in addition to flowing through contraction/expansion regions. For example, a microfluidic mixing device 340 having four (4) contraction/expansion regions and two flow reversal regions is illustrated in FIGS. 12A–12B. The device 340 is constructed in eleven layers 341–351, including stencil layers 342, 344, 346, 348, 350. Starting from the bottom, the first layer 341 defines two fluid inlet ports 355, 356, each port being about one hundred twenty (120) mils in diameter. The second layer 342 defines two inlet channel sections 357, 358 meeting at a junction channel 360. The third, fifth, seventh, and ninth layers 343, 345, 347, 349 each define a small aperture 362, 364, 366, 368, respectively. Each of the apertures 362, 364, 366, 368 are about ten (10) mils in diameter and are preferably substantially centered along the width of their surrounding channels. The fourth, sixth, and eighth layers 344, 346, 348 each define a channel 363, 365, 367, respectively. The tenth layer 350 defines an outlet channel 370 that leads to the fluidic outlet port 372 defined in the eleventh layer 351. Each of the above-described channels has a nominal width of about one hundred twenty (120) mils. As described previously, the stencil layers 342, 344, 346, 348, 350 may be advantageously fabricated from double-sided self-adhesive tapes, while the sandwiching non-stencil layers 341, 343, 345, 347, 349, 351 may be advantageously fabricated from non-adhesive materials.

In operation, a first fluid stream is injected into the first inlet port 355 and a second fluid stream is injected into the second inlet port 356. The fluid streams travel through channel sections 357, 358, respectively until they meet at a junction channel 360. From the junction channel 360, the components of the combined stream flow through the first aperture 362 into the first short channel 363, the combination serving as a first contraction/expansion region. From the first short channel 363, the fluid combination flows through the second aperture 364 into the second short channel 365. Notably, the second short channel segment 365 reverses the direction of the fluid combination by approximately 180 degrees toward the third aperture 366. From the third aperture 366, the fluid enters the third short channel 367, where the fluid changes direction again toward the fourth aperture 368. Looking from the top down, the fluid would appear to move in a back-and-forth direction between the second short channel 365 and the third short channel 367. From the fourth aperture 368, the fluid flows into the outlet channel 370 and ultimately exits the device 340 through the outlet port 372. The resulting mixing device 340 utilizes many (eleven) layers but promotes mixing between two microfluidic streams within a small footprint, as shown in top view in FIG. 12B.

EXAMPLE 9

Further microfluidic mixing device embodiments having multiple contraction/expansion regions and many fluid directional changes may be constructed. For example, a microfluidic mixing device 380 having eighteen (18) contraction/expansion regions and sixteen roughly ninety-degree directional change regions is illustrated in FIGS. 13A–13B. The device 380 is constructed in five layers 381–385, including stencil layers 382, 384. Starting from the bottom, the first layer 381 defines two fluid inlet ports 386, 387 and two outlet ports 388, 389, each port being about eighty (80) mils in diameter. The second layer 382 defines two inlet channel sections 392, 393 meeting at a junction channel 395. The second layer 382 defines eight parallel short channels 397 and another channel 398 having a splitting region for dividing a mixed fluid stream into two substreams. The third layer 383 defines eighteen (18) small apertures 399, each aperture 399 being about six (6) mils in diameter. These apertures 399 are substantially centered along the width of each of the surrounding channels 397, 400. The fourth layer 400 defines ten short channels 400, each of which slightly overlaps two channels defined in the second layer 382. Each of channels 397, 400 is downstream of one aperture 399 and upstream of another aperture 399. The fifth layer 385 may be fabricated from a bare substrate or film, thus serving to enclose the channel sections 400 from above and support the device 380 if necessary. The fifth layer 305 may be fabricated from a bare substrate or film, thus serving to enclose the channel sections 320 from above and support the device 300 if necessary. Each of the above-described channels has a nominal width of about forty (40) mils. As described in connection with the previous two Examples, the stencil layers 382, 384 may be advantageously fabricated from double-sided self-adhesive tapes, while the sandwiching layers 381, 383, 385 may be advantageously fabricated from non-adhesive materials.

The mixing device 380 operates similarly to the mixers described in the preceding few Examples. A first fluid stream is injected into the first inlet port 386 and a second fluid stream is injected into the second inlet port 387. The fluid streams travel through channel sections 393, 393, respectively until they meet at junction channel 395. From the junction 395, the combined stream flows through the eighteen expansion-contraction regions and changes direction sixteen times, each time by approximately ninety (90) degrees before splitting into two substreams at channel 398 and exiting the device through outlet ports 388, 389. Increased flowrate through the device 380 seems to promote better mixing, as shown in FIGS. 13C–13E. FIGS. 13C–13E show mixing between two fluids at a combined flow rates of twenty (20), two hundred (200), and four hundred (400) microliters per minute, respectively. As is apparent from comparing the three figures, more rapid or complete mixing within a given length of device is yielded at higher fluid flow rates.

EXAMPLE 10

In one embodiment, a microfluidic mixing device includes an upstream channel, a downstream channel, and spacer layer defining an aperture configured in the shape of a slit that is disposed substantially perpendicular to the direction of fluid flow downstream of the overlap region. One example of a microfluidic mixer embodying such a design is shown in FIGS. 14A–14B. A mixing device 410 is constructed in five layers 411–415, including two stencil layers 412, 414. Starting from the bottom, the first layer 411 defines two fluid inlet ports 417, 418 and one outlet port 419, each port being about sixty (60) mils in diameter. The second layer 412 defines two inlet channel sections 421, 422 meeting at a junction 423 that feeds an upstream channel section 424. The second layer 412 also defines a via 426. The third layer 413 defines a narrow slit 428 that is disposed lengthwise substantially parallel to the length of the upstream channel section 424, and substantially perpendicular to the downstream channel 432. The slit 428 is preferably constructed without removing material by cutting the third layer 413 with a blade such as a computer-controlled plotter modified to manipulate a cutting blade. Alternatively, the slit 428 may be formed by laser cutting, die cutting, or other equivalent means. Preferably, the slit 428 is substantially centered along the width of the inlet channel section 424. The fourth layer 414 defines an outlet channel 432 that is oriented substantially perpendicular to and slightly overlaps the inlet channel section 424. The fifth layer 415 serves to enclose the channel 432 from above, and may further be used to provide structural support to the device 410. The various channels of the device 410 each have a nominal width of about forty (40) mils. The various layers 411–415 may be assembled into a substantially sealed device 410 using adhesives or other equivalent means to fasten the layers together and prevent unwanted fluid leakage. If adhesives are used, then the second and fourth stencil layers 412, 414 are preferably constructed from double-sided self-adhesive materials as described previously.

In operation, a first fluid stream is injected into the first inlet port 417 and a second fluid stream is injected into the second inlet port 418. The fluid streams travel through channel sections 421, 422, respectively until they meet at a junction 423 that feeds an upstream channel section 424. In the upstream channel section 424, the two fluids flow side-by-side in a substantially unmixed combined stream until reaching the slit 428. As the combined stream passes from the upstream channel section 424 through the slit 428, the combined stream turns ninety (90) degrees and is "folded" into the downstream channel 432 such that, immediately downstream of the slit 428, the first fluid fills the lower portion of the downstream channel 432 and the second fluid forms a fluid layer on top of the first fluid and fills the upper portion of the downstream channel 432. Since the fourth stencil layer 414 may be fabricated from very thin materials, typically well under ten (10) mils thick (e.g., a one (1) mil thick polypropylene film having a 2.4 mil thick integral layer rubber-based pressure-sensitive adhesive on both sides (Avery Dennison, Brea, Calif.) totaling a combined thickness of 5.8 mils), the width of the 40-mil-wide channel 432 is much greater than its height and a large interfacial contact area between the two fluid streams is established. As discussed previously, a side benefit of layering a first fluid in a thin sheet above a second fluid is that it reduces the average and maximum diffusion lengths, thus promoting more rapid mixing. From the downstream channel 432, the fluidic mixture flows through two vias 430, 426 before exiting the device 410 through outlet port 419.

Interaction between two fluids provided to the device 410 is illustrated in FIG. 14C. A light-colored first fluid stream 432 is supplied to the first channel section 421, and a dark-colored second fluid stream 431 is supplied to the second channel section 422. At the junction 423, the two fluids streams 431, 432 meet but do not mix, forming a boundary 433 that persists along the entire length of the upstream channel section 424 until the fluid combination flows through the slit 428. Downstream of the slit 428, the combined stream is "folded" such that the first fluid stream 432A fills the lower portion of the downstream channel 432 and the second fluid stream 431A fills the upper portion of the downstream channel 432. So configured, the two fluid streams 431A, 432A mix rapidly within the downstream channel 432 until a substantially homogeneous fluid mixture 435 results.

EXAMPLE 11

In another embodiment, a microfluidic mixer having overlapping channels includes multiple apertures for communicating fluid from a first channel to a second channel. One example of a microfluidic mixer embodying such a design is shown in FIGS. 15A–15B. A mixing device 440 is constructed in five layers 441–445, including two stencil layers 442, 444. Starting from the bottom, the first layer 441 defines two fluid inlet ports 447, 448 and one outlet port 449, each port being about sixty (60) mils in diameter. The second layer 442 defines two vias 453, 454 and a first upstream channel 450 that terminates at a wide region 451. The third layer 443 defines two vias 455, 456 and multiple small apertures 458 arranged in a line and positioned above the wide region 451. The illustrated device 440 has five such apertures each being about six (6) mils in diameter. The fourth layer 444 defines a second upstream channel 460, a wide region 461 disposed above the overlapping wide region 451 in the second layer 442, and a downstream channel 462. The fifth layer 445 lacks any structural features but serves to enclose the channel structures in the fourth layer 444, and further may provide general support to the device 440. Each of the channels 450, 460, 462 have a nominal width of about forty (40) mils, and the wide regions 451, 461 are each about one hundred sixty (160) mils wide.

In use, a first fluid stream is injected into the first inlet port 448 and a second fluid stream is injected into the second fluid inlet port 447. The first fluid stream flows through the first upstream channel 450 to the first wide channel region 451. At the same time, the second fluid stream flows through the second upstream channel 460 to the second wide channel region 461. The first fluid stream flows from the first wide channel region 451 through the multiple small apertures 458 and into the second wide channel region 461 to join the second fluid stream. By virtue of flowing through the multiple small apertures 458, the first fluid is divided into several substreams that appear as "streaks" in the second fluid in the wide region 461 and ensuing downstream channel 462. These streaks provide a large interfacial contact area between the two fluids that promotes mixing. It has been found that increasing the number of small apertures, thus increasing the number of streaks, promotes more rapid and complete mixing within a given distance of the overlap region. For example, FIG. 15C is a photograph a streak-type mixing device constructed according to the design of FIGS. 15A–15B but having only three 6-mil small apertures 458. At a combined fluid flow of about twenty (20) microliters per minute, mixing is apparent between the two fluids but not particularly complete. In contrast, FIG. 15D illustrates a streak-type mixing device that is substantially identical except for the inclusion of seven 6-mil small apertures 458 in the overlap region. At a combined fluid flow rate of about twenty (20) microliters per minute, it is apparent mixing between the fluid streams is much improved compared to the preceding case. Both devices of FIGS. 15C–15D were constructed using one (1) mil thick polypropylene film having a 2.4 mil thick integral layer rubber-based pressure-sensitive adhesive on both sides (Avery Dennison, Brea, Calif.) for the second and fourth stencil layers 442, 444 and adhesiveless 2-mil thickness polypropylene for the remaining layers 441, 443, 445. In each case the various fluid structures were defined using a computer-controlled laser cutter, and after careful alignment of the layers 441–445 they were pressed together to yield substantially sealed microstructures.

EXAMPLE 12

In another embodiment, a streak-type microfluidic mixer may be constructed from rigid materials using surface micromachining techniques, such as the technique described previously in connection with Example 4. Referring to FIGS. 16A–16B, a mixing device 500 is constructed from three substrates 501–503. An inlet/outlet channel 515, 516 is patterned in the lower surface 505 of a first <110> Si substrate 501 using an oxide mask and etched in an appropriate etching solution. The inlet/outlet channel 515, 516 is etched to that it is about 100 microns wide and about 3 microns deep. A second channel 519 is similarly etched in the upper surface 504 of the third substrate 503. Ports (large holes about 800 microns in diameter) 511–513 are drilled through the first substrate 501, and multiple small holes 518 are drilled or otherwise micromachined (e.g., etched) through the second substrate 502. Preferably, the small holes 518 are arranged in a line substantially perpendicular to the direction of bulk fluid flow in the outlet channel 516, and the small holes are each less than about ten, more preferably less than about six, mils in diameter. The three substrates 501–503 are aligned face-to-face sandwiching the central substrate 502, and the respective layers are anodically or otherwise bonded together to form a substantially sealed microfluidic mixing device 500 as shown in top view in FIG. 16B.

In use, the device 500 operates similarly to the device 440 discussed in the previous Example. A first fluid stream is injected into the first inlet port 512 and into the inlet channel 515 upstream of the small apertures 518. A second fluid stream is injected into the second inlet port 515 and into the second inlet channel 519, also upstream of the small apertures 518. The two inlet channels 515, 519 partially overlap, but fluid communication between the channels is provided solely through the small apertures 518. As the second fluid flows through the small apertures 518 to join the first fluid, it forms several streaks in the first fluid in the outlet channel 516. These streaks provide a large interfacial contact area between the two streams that promotes mixing. It is expected that using a larger number of small apertures 518 will provide better mixing utility than using a small number of such apertures.

The present invention described and claimed herein is not to be limited in scope by the specific embodiments herein disclosed, since these embodiments are intended merely to illustrate certain aspects of the invention. All equivalent embodiments are intended to be within the scope of this invention. Indeed, various modifications of the invention in addition to those shown and described herein will become apparent to those skilled in the art from the foregoing description. For example, other materials and configurations not specifically disclosed herein are also contemplated. Such modifications are also intended to fall within the scope of the appended claims.

The disclosures of all references cited herein are incorporated by reference in their entireties.

What is claimed is:

1. A microfluidic device for mixing a plurality of fluid streams, the mixing device comprising:
a plurality of microfluidic inlet channels that merge into a microfluidic junction channel, the junction channel being defined in a first device layer and having a characteristic cross-sectional area; and
a plurality of contraction/expansion regions in fluid communication with the junction channel and arranged in series, each contraction/expansion region including:
an aperture defined in a second device layer, the aperture having a characteristic cross-sectional area that is substantially smaller than the area of the junction channel; and
a microfluidic expansion channel defined in either the first device layer or a third device layer, the expansion channel having a characteristic cross-sectional area that is substantially larger than the area of the aperture.

2. The mixing device of claim 1 wherein each aperture is less than about 250 microns in major dimension.

3. The mixing device of claim 2 wherein:
the junction channel contains a stream of multiple fluids;
upstream of an aperture, the stream of multiple fluids flows in substantially a first direction;
downstream of an aperture, the stream of multiple fluids flows in substantially a second direction that is substantially different from the first direction.

4. The mixing device of claim 3 wherein the second direction is at least about 90 degrees apart from the first direction.

5. The mixing device of claim 1 wherein any of the inlet channels, junction channel, or expansion channels are defined through the entire thickness of a stencil layer.

6. The mixing device of claim 1 wherein any of the inlet channels, junction channel, or expansion channels are defined in a surface but do not penetrate the entire thickness of a device layer.

7. The mixing device of claim 6 wherein any of the inlet channels, junction channel, or expansion channels are defined using one or more surface micromachining techniques.

8. The mixing device of claim 1 wherein the device is formed with multiple layers, and the various layers are bonded or fastened together.

9. The mixing device of claim 8 wherein the bonded or fastened layers form a substantially sealed device.

10. A multi-layer microfluidic mixing device comprising:
a first device layer, a third device layer, and a second device layer disposed between the first device layer and the third device layer;
a plurality of microfluidic inlet channels that merge into a junction channel, the junction channel being defined in the first device layer and having a characteristic width;
a slit defined in the second device layer, the slit having a characteristic length and width and being disposed lengthwise in a direction substantially parallel to the junction channel, the slit length being substantially greater than the slit width; and
a microfluidic outlet channel defined in the third device layer and having a characteristic width, the outlet channel being disposed in a direction substantially perpendicular to both the junction channel and the slit;
wherein the slit is disposed between and in fluid communication with the junction channel and the outlet channel, the slit width is substantially smaller than the junction channel width, and the slit width is substantially smaller than the outlet channel width.

11. The mixing device of claim 10 wherein the slit length is at least as great as the outlet channel width.

12. The mixing device of claim 10 wherein the first device layer is a first stencil layer, the third device layer is a third stencil layer, the junction channel is defined through the entire thickness of the first stencil layer, and the outlet channel is defined through the entire thickness of the third stencil layer.

13. The mixing device of claim 10 wherein the junction channel is defined in a surface of but does not penetrate the entire thickness of the first device layer and the outlet channel is defined in a surface of but does not penetrate the entire thickness of the third device layer.

14. The mixing device of claim 10 herein any of the plurality of inlet channels, the junction channel, or the outlet channel is defined using one or more surface micromachining techniques.

15. The mixing device of claim 10 wherein the junction channel is substantially upstream of the slit, and the outlet channel is substantially downstream of the slit.

16. The mixing device of claim 10 wherein first device layer, second device layer, and third device layer are bonded or fastened together to form a substantially sealed device.

17. A microfluidic mixing device comprising:
   a first device layer, a second device layer, and a third device layer disposed between the first device layer and the second device layer;
   a first microfluidic channel defined in the first device layer, the first channel having a characteristic width;
   a second microfluidic channel defined in the second device layer, the second channel having a characteristic width ; and
   a plurality of apertures defined in the third device layer, the plurality of apertures being disposed between and in fluid communication with the first channel and the second channel, each aperture of the plurality of apertures having a major dimension that is substantially smaller than each of the width of the first channel and the width of the second channel.

18. The mixing device of claim 17 wherein the width of the first channel is substantially equal to the width of the second channel.

19. The mixing device of claim 18 wherein the major dimension of each aperture of the plurality of apertures is less than about one-quarter of each of the width of the first channel and the width of the second channel.

20. The mixing device of claim 18 wherein each aperture has a major dimension of less than about 200 microns.

21. The mixing device of claim 18 wherein each aperture has a major dimension of less than about 100 microns.

22. The mixing device of claim 17 wherein the first channel has a characteristic cross-sectional area, the second channel has a characteristic cross-sectional area, each aperture has a characteristic cross-sectional area, and the area of each aperture is substantially smaller than the area of the first channel and the area of the second channel.

23. The mixing device of claim 17 wherein the first channel is substantially upstream of the plurality of apertures and the second channel is substantially downstream of the plurality of apertures.

24. The mixing device of claim 17 wherein the first device layer is a first stencil layer with the first channel being defined through the entire thickness of the first stencil layer and the second device layer is a second stencil layer with the second channel being defined through the entire thickness of the second stencil layer.

25. The mixing device of claim 17 wherein:
   the first channel is defined in a surface of the first device layer but does not penetrate the entire thickness of the first device layer; and
   the second channel is defined in a surface of the second device layer but does not penetrate the entire thickness of the second device layer.

26. The mixing device of claim 25 wherein any of the first channel or the second channel are defined using one or more surface micromachining techniques.

27. The mixing device of claim 17 wherein the first device layer, second device layer, and third device layer are bonded or fastened together.

28. The mixing device of claim 17 further comprising a fourth device layer and a fifth device layer, wherein the first through fifth device layers are bonded or fastened together to form a substantially sealed device.

* * * * *